US009295828B2

(12) United States Patent
Halperin et al.

(10) Patent No.: US 9,295,828 B2
(45) Date of Patent: Mar. 29, 2016

(54) SELF-RESONANT INDUCTOR WOUND PORTION OF AN IMPLANTABLE LEAD FOR ENHANCED MRI COMPATIBILITY OF ACTIVE IMPLANTABLE MEDICAL DEVICES

(71) Applicant: Greatbatch Ltd., Clarence, NY (US)

(72) Inventors: Henry R. Halperin, Pikesville, MD (US); Robert A. Stevenson, Canyon County, CA (US); Kishore Kumar Kondabatni, Arcadia, CA (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/680,083

(22) Filed: Nov. 18, 2012

(65) Prior Publication Data

US 2013/0073021 A1 Mar. 21, 2013

Related U.S. Application Data

(63) Continuation-in-part of application No. 12/891,292, filed on Sep. 27, 2010, now Pat. No. 8,437,865.

(51) Int. Cl.
*A61N 1/05* (2006.01)
*G01R 33/36* (2006.01)
(Continued)

(52) U.S. Cl.
CPC .............. *A61N 1/05* (2013.01); *G01R 33/3685* (2013.01); *A61B 2018/00839* (2013.01); *A61B 2019/5236* (2013.01); *A61N 2001/086* (2013.01)

(58) Field of Classification Search
CPC ....... A61N 1/05; A61N 1/056; A61N 1/0551; A61N 1/3718; A61N 2001/086
USPC ........................................................ 607/116
See application file for complete search history.

(56) References Cited

U.S. PATENT DOCUMENTS 3,871,382 A  3/1975 Mann
3,968,802 A  7/1976 Ballis
(Continued)

FOREIGN PATENT DOCUMENTS

EP  0243573  11/1987
EP  0145430  5/1991
(Continued)

OTHER PUBLICATIONS

Ariel Roguin et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

(Continued)

*Primary Examiner* — Christopher D Koharski
*Assistant Examiner* — Michael D Abreu
(74) *Attorney, Agent, or Firm* — Michael F. Scalise

(57) ABSTRACT

An implantable lead includes a lead conductor having a length extending from a proximal end to a distal end. A self-resonant inductor is connected in series along a portion of the length of the lead conductor. The self-resonant inductor includes a single length of conductive material including a dielectric coating substantially surrounding the single length of conductive material. The self-resonant inductor includes a first coiled or spiral conductor disposed along an inductor section spanning in a first direction from a first location to a second location. A second coiled or spiral conductor is disposed along the inductor section spanning in a second direction from the second location to the first location, where the second direction is opposite the first direction. A third coiled or spiral conductor is disposed along the inductor section spanning in the first direction from the first location to the second location.

70 Claims, 18 Drawing Sheets

(51) Int. Cl.
  *A61B 18/00* (2006.01)
  *A61B 19/00* (2006.01)
  *A61N 1/08* (2006.01)

(56) References Cited

U.S. PATENT DOCUMENTS

| | | |
|---|---|---|
| 3,980,975 A | 9/1976 | Maxon, Jr. et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,354,880 A | 10/1982 | Adams et al. |
| 4,424,551 A | 1/1984 | Stevenson et al. |
| 4,431,005 A | 2/1984 | McCormick |
| 4,437,474 A | 3/1984 | Peers-Trevarton |
| 4,445,501 A | 5/1984 | Bresler |
| 4,572,198 A | 2/1986 | Codrington |
| 4,585,001 A | 4/1986 | Belt |
| 4,633,181 A | 12/1986 | Muphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thomander et al. |
| 4,746,864 A | 5/1988 | Satoh |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,839,594 A * | 6/1989 | Misic et al. .................. 324/318 |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,977,298 A | 7/1990 | Sholder |
| 4,960,106 A | 10/1990 | Kubokawa |
| 4,989,608 A | 2/1991 | Ratner |
| 4,991,580 A | 2/1991 | Moore |
| 5,019,075 A | 5/1991 | Spears et al. |
| 5,044,375 A | 9/1991 | Bach, Jr. et al. |
| 5,052,404 A | 10/1991 | Hodgson |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Sharman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,333,095 A | 7/1994 | Stevenson et al. |
| 5,334,045 A | 8/1994 | Cappa et al. |
| 5,334,193 A | 8/1994 | Nardelia |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinciarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,451,232 A | 9/1995 | Rinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,629,622 A | 5/1997 | Scampini |
| 5,662,108 A | 9/1997 | Budd et al. |
| 5,682,897 A | 11/1997 | Pomeranz |
| 5,685,878 A | 11/1997 | Falwell et al. |
| 5,697,958 A | 12/1997 | Paul et al. |
| 5,699,801 A | 12/1997 | Atalar et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,887 A | 4/1998 | Barreras et al. |
| 5,741,321 A | 4/1998 | Brennen |
| 5,751,539 A | 5/1998 | Stevenson et al. |
| 5,759,202 A | 6/1998 | Schroeppel |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,824,026 A | 10/1998 | Diaz |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,864,234 A | 1/1999 | Ludeke |
| 5,868,674 A | 2/1999 | Glowinski et al. |
| 5,879,347 A | 3/1999 | Saadat |
| 5,891,134 A | 4/1999 | Goble et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,959,829 A | 9/1999 | Stevenson et al. |
| 5,964,705 A | 10/1999 | Truwit et al. |
| 5,970,604 A | 10/1999 | Person et al. |
| 5,973,906 A | 10/1999 | Stevenson et al. |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,052,614 A | 4/2000 | Morris, Sr. et al. |

(56) References Cited

U.S. PATENT DOCUMENTS

| | | |
|---|---|---|
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,141,594 A | 10/2000 | Flynn et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Ludeke et al. |
| 6,238,390 B1 | 5/2001 | Tu et al. |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,473,291 B1 | 10/2002 | Stevenson |
| 6,486,529 B2 | 11/2002 | Chi et al. |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboae et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindegren et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,771,067 B2 | 8/2004 | Kellman et al. |
| 6,795,730 B2 | 9/2004 | Connelly et al. |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Froberg et al. |
| 6,949,929 B2 | 9/2005 | Gray et al. |
| 6,950,696 B2 | 9/2005 | Bjoring et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,999,818 B2 | 2/2006 | Stevenson et al. |
| 7,012,192 B2 | 3/2006 | Stevenson et al. |
| 7,013,180 B2 | 3/2006 | Villaseca et al. |
| 7,015,393 B2 | 3/2006 | Weiner et al. |
| 7,038,900 B2 | 5/2006 | Stevenson et al. |
| 7,039,455 B1 | 5/2006 | Brosovich et al. |
| 7,047,073 B2 | 5/2006 | Hoijer et al. |
| 7,050,855 B2 | 5/2006 | Zeijlemaker et al. |
| 7,091,412 B2 | 8/2006 | Wang et al. |
| 7,092,766 B1 | 8/2006 | Salys et al. |
| 7,113,387 B2 | 9/2006 | Stevenson et al. |
| 7,123,013 B2 | 10/2006 | Gray |
| 7,127,294 B1 | 10/2006 | Wang et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin |
| 7,162,302 B2 | 1/2007 | Wang et al. |
| 7,164,950 B2 | 1/2007 | Kroll et al. |
| 7,174,219 B2 | 2/2007 | Wahlstrand et al. |
| 7,236,816 B2 | 6/2007 | Kumar et al. |
| 7,276,474 B2 | 10/2007 | Marchant et al. |
| 7,310,216 B2 | 12/2007 | Stevenson et al. |
| 7,319,905 B1 | 1/2008 | Morgan et al. |
| 7,363,090 B2 | 4/2008 | Halperin |
| 7,369,898 B1 | 5/2008 | Kroll et al. |
| 7,388,378 B2 | 6/2008 | Gray et al. |
| 7,422,568 B2 | 9/2008 | Yang et al. |
| 7,511,921 B2 | 3/2009 | Mallary et al. |
| 7,529,590 B2 | 5/2009 | MacDonald |
| 7,561,906 B2 | 7/2009 | Atalar et al. |
| 7,689,288 B2 | 3/2010 | Stevenson et al. |
| 7,702,387 B2 | 4/2010 | Stevenson et al. |
| 7,729,770 B2 | 6/2010 | Cabelka et al. |
| 7,839,146 B2 | 11/2010 | Gray |
| 7,844,343 B2 | 11/2010 | Wahlstrand et al. |
| 7,899,551 B2 | 3/2011 | Westlund et al. |
| 8,301,249 B2 | 10/2012 | Min et al. |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013928 A1 | 1/2003 | Russell |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1* | 3/2003 | Susil et al. ............ 600/424 |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker et al. |
| 2003/0144719 A1 | 7/2003 | Zeijlemaker |
| 2003/0144720 A1* | 7/2003 | Villaseca et al. ............ 607/122 |
| 2003/0144721 A1 | 7/2003 | Villaseca et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2004/0015079 A1 | 1/2004 | Berger et al. |
| 2004/0034338 A1 | 2/2004 | Thierfelder et al. |

(56) References Cited

U.S. PATENT DOCUMENTS

| | | |
|---|---|---|
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |
| 2004/0249428 A1 | 12/2004 | Wang et al. |
| 2004/0263173 A1* | 12/2004 | Gray .................... 324/322 |
| 2004/0263174 A1 | 12/2004 | Gray et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2006/0009819 A1 | 1/2006 | Przybyszewski |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand et al. |
| 2006/0211979 A1 | 9/2006 | Smith et al. |
| 2006/0229693 A1 | 10/2006 | Bauer et al. |
| 2006/0247684 A1 | 11/2006 | Halperin |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179577 A1 | 8/2007 | Marshall et al. |
| 2007/0208383 A1 | 9/2007 | Williams |
| 2007/0250743 A1 | 10/2007 | Matsubara et al. |
| 2007/0255332 A1 | 11/2007 | Cabelka |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson |
| 2008/0051854 A1 | 2/2008 | Bulkes et al. |
| 2008/0071313 A1 | 3/2008 | Stevenson |
| 2008/0116997 A1 | 5/2008 | Dabney |
| 2008/0132986 A1 | 6/2008 | Gray et al. |
| 2008/0132987 A1 | 6/2008 | Westlund |
| 2008/0161886 A1 | 7/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0243218 A1 | 10/2008 | Bottomley et al. |
| 2008/0262584 A1 | 10/2008 | Bottomley et al. |
| 2008/0262592 A1 | 10/2008 | Jordan et al. |
| 2008/0269591 A1 | 10/2008 | Halperin et al. |
| 2009/0099440 A1 | 4/2009 | Vohl |
| 2009/0099555 A1 | 4/2009 | Vohl et al. |
| 2009/0163980 A1 | 6/2009 | Stevenson |
| 2009/0243756 A1 | 10/2009 | Stevenson et al. |
| 2009/0281592 A1 | 11/2009 | Vase |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0076538 A1 | 3/2010 | Desai et al. |
| 2010/0100164 A1 | 4/2010 | Johnson et al. |
| 2010/0114276 A1 | 5/2010 | Min et al. |
| 2010/0114277 A1* | 5/2010 | Zhao et al. ............. 607/116 |
| 2010/0138192 A1 | 6/2010 | Min |
| 2010/0160989 A1 | 6/2010 | Legay |
| 2010/0160997 A1 | 6/2010 | Johnson et al. |
| 2010/0174348 A1 | 7/2010 | Bulkes et al. |
| 2010/0174349 A1 | 7/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak, III |
| 2011/0043297 A1 | 2/2011 | Stevenson et al. |
| 2011/0079423 A1* | 4/2011 | Zhao et al. ............. 174/5 R |
| 2011/0196460 A1* | 8/2011 | Weiss .................... 607/116 |

FOREIGN PATENT DOCUMENTS

| | | |
|---|---|---|
| EP | 466424 | 1/1992 |
| EP | 557127 | 8/1993 |
| EP | 0673621 | 9/1995 |
| EP | 0498996 | 3/1997 |
| EP | 0930509 | 12/1998 |
| EP | 1021730 | 4/1999 |
| EP | 1469910 | 12/2006 |
| EP | 2025361 | 11/2007 |
| EP | 1883449 | 1/2009 |
| JP | 60141034 | 7/1985 |
| JP | 61181925 | 8/1985 |
| JP | 62233905 | 10/1987 |
| JP | 4071536 | 3/1992 |
| JP | 6054823 | 3/1994 |
| JP | 6199470902 | 3/1994 |
| JP | 994238 | 4/1997 |
| JP | 11239572 | 9/1999 |
| WO | 87/04080 | 7/1987 |
| WO | 92/10213 | 6/1992 |
| WO | 94/23782 | 10/1994 |
| WO | 97/40396 | 10/1997 |
| WO | 98/52461 | 11/1998 |
| WO | 99/19739 | 4/1999 |
| WO | 00/10456 | 3/2000 |
| WO | 00/25672 | 5/2000 |
| WO | 02/083016 | 10/2002 |
| WO | 03037424 | 5/2003 |
| WO | 03063946 | 8/2003 |
| WO | 03063952 | 8/2003 |
| WO | 03063953 | 8/2003 |
| WO | 03063955 | 8/2003 |
| WO | 03063956 | 8/2003 |
| WO | 03063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |

OTHER PUBLICATIONS

Roger Christoph Luchinger, Safety Aspects of Cardiac Pacemakers in Magnetic Resonance Imaging, a dissertation submitted to the Swiss Federal Institute of Technology Zurich, Zurich, Switzerland, 2002.

(56) References Cited

OTHER PUBLICATIONS

C. Gabriel, S. Gabriel and E. Cortout, I. Dielectric Properties of Biological Tissues: Literature Survey.
S. Gabriel, R.W. Lau and C. Gabriel, II. Dielectric Properties of Biological Tissues: Measurements and the Frequency Range 0Hz to 20 GHz.
S. Gabriel, R.W. Lau and C. Gabriel, III. Dielectric Properties of Biological Tissues: Parametric Models for the Dielectric Spectrum of Tissues.
Constatine A. Balanis, Advanced Engineering Electromagnetics, John Wiley & Sons, Inc., 1989.
Robert C. Susil, Christopher J. Yeung, Henry R. Halperin, Albert CL. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.
Robert C. Susil, Ergin Atalar, Albert Lardo, Multifunctional Interventional Devices for Use in MRI, U.S. Appl. No. 60/283,725, filed Apr. 13, 2001.
European Search Report dated Oct. 10, 2012.
European Search Report dated Sep. 19, 2012.
Mauritis K. Konings, Lambertus W. Bartels, Henk F.M. Smits and Chris J.G. Bakker, "Heating around Intravascular Guidewires by Resonating RF Waves," Journal of Magnetic Resonance Imaging, 12:79-85, 2000.
Michael J. Weiner, Wilson Greatbatch, Patrick R. Connelly, U.S. Appl. No. 60/269,817, filed Feb. 20, 2001, entitled "Electromagnetic Interference Immune Cardiac Assist System."
Wes Clement et al., "Estimation of Effective Lead Loop Area for Implantable Pulse Generators and Implantable Cardioverter Defibriallators," AAMI EMC Task Force, Apr. 12, 2004, 10 pages.
Frank G. Shellock, Ph.D. "MRI Issues for Neuromodulation Devices," Institute for Magnetic Resonance Safety, Education, and Research (IMRSER).
R.S. Johnson et al., Characterization of the Relationship between M-Induced Distal tip Heating in Cardiac Pacing Leads and the Electrical Performance of Novel Filtered Tip Assemblies; 17th Scientific Meeting & Exhibition of the INternational Society for Magnetic Resonance in Medicine, Honolulu, Hawaii, Apr. 18-24, 2009, Page No. 307.
F.G. Shellock et al., Comparative Analysis of MR-Inducing Distal Heating in Novel Filtered Cardiac Pacing Leads Using Two Geometric Configurations; 17th Scientific Meeting & Exhibition of the International Society for Magnetic Resonance in Medicine, Honolulu, Hawaii, Apr. 18-24, 2009, Page No. 3104.
G.D. Wilk et al, High-k Gate Dielectrics: Current Status and Materials Properties Considerations, Journal of Applied Physics, vol. 89, No. 10, May 15, 2001, pp. 5243-5275, 2001 American Physics.

* cited by examiner $$fr = \frac{1}{2\pi\sqrt{LC}}$$

Where:  fr = resonant frequency
        L = inductance in henries
        C = capacitance in farads Solving for C:                    Solving for L:

$$C = \frac{1}{(fr)^2 (2\pi)^2 L}$$          $$L = \frac{1}{(fr)^2 (2\pi)^2 C}$$

→ assume a 1.5 Tesla MRI System,
    then the RF pulsed frequency = 64 MHz

→ assume that L = 1 nanohenry ($1 \times 10^{-9}$)

then; $C = \dfrac{1}{(64 \times 10^6)^2 (2\pi)^2 (1 \times 10^{-9})}$ or;  C = $6.18 \times 10^{-9}$ f   (6.18 nanofared)

FIG. 14    $z_{ab} = \dfrac{(j\omega L)(-j/\omega C)}{(j\omega L - j/\omega C)}$ FIG. 15    $X_L = +j(2\pi fL) = +j\omega L$
$X_C = -j\left(\dfrac{1}{2\pi fC}\right) = \dfrac{-j}{\omega C}$

SELF-RESONANT INDUCTOR WOUND PORTION OF AN IMPLANTABLE LEAD FOR ENHANCED MRI COMPATIBILITY OF ACTIVE IMPLANTABLE MEDICAL DEVICES

CROSS-REFERENCE TO RELATED APPLICATIONS

This application claims priority to and is a continuation-in-part of U.S. application Ser. No. 12/891,292, filed on Sep. 27, 2010, now U.S. Pat. No. 8,437,865, the contents of which are incorporated herein by reference.

DESCRIPTION

1. Field of the Invention

The present invention generally relates to medical leads, probes or catheters for surgery or implantation. More particularly, the present invention relates to a multilayer inductor connected in series along the lead, probe or catheter.

2. Background of the Invention

This invention relates generally to novel EMI tank filter assemblies, particularly of the type used in active medical devices (AMDs) such as cardiac pacemakers, cardioverter defibrillators, neurostimulators, externally worn Holter monitors and the like, which decouple lead wires and/or electronic components of the medical device from undesirable electromagnetic interference (EMI) signals at a selected frequency or frequencies, such as the RF pulsed fields of Magnetic Resonance Imaging (MRI) equipment.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:

(1) "Safety Aspects of Cardiac Pacemakers in Magnetic Resonance Imaging", a dissertation submitted to the Swiss Federal Institute of Technology Zurich presented by Roger Christoph Luchinger, Zurich 2002;

(2) "I. Dielectric Properties of Biological Tissues: Literature Survey", by C. Gabriel, S. Gabriel and E. Cortout;

(3) "II. Dielectric Properties of Biological Tissues: Measurements and the Frequency Range 0 Hz to 20 GHz", by S. Gabriel, R. W. Lau and C. Gabriel;

(4) "III. Dielectric Properties of Biological Tissues: Parametric Models for the Dielectric Spectrum of Tissues", by S. Gabriel, R. W. Lau and C. Gabriel; and (5) "Advanced Engineering Electromagnetics, C. A. Balanis, Wiley, 1989;

(6) Systems and Methods for Magnetic-Resonance-Guided Interventional Procedures, Patent Application Publication US 2003/0050557, Susil and Halperin et. al, published Mar. 13, 2003;

(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and (8) Multifunctional Interventional Devices for Use in MRI, U.S. patent application Ser. No. 60/283,725, filed Apr. 13, 2001. The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the International Society for Magnetic Resonance in Medicine (ISMRM), which was held on 5 and 6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies with the field strength of the main static field where: RF PULSED FREQUENCY in MHz=(42.56) (STATIC FIELD STRENGTH IN TESLA).

The third type of electromagnetic field is the time-varying magnetic gradient fields designated $B_1$ which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and EMI are induced into an implanted lead wire system. At very low frequency (VLF), voltages are induced at the input to the cardiac pacemaker as currents circulate throughout the patient's body and create voltage drops. Because of the vector displacement between the pacemaker housing and, for example, the TIP electrode, voltage drop across the resistance of body tissues may be sensed due to Ohms Law and the circulating current of the RF signal. At higher frequencies, the implanted lead wire systems actually act as antennas where currents are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the lead wire system (for example, at the header block of a cardiac pacemaker). This has to do with the wavelength of the signals involved and where they couple efficiently into the system.

Magnetic field coupling into an implanted lead wire system is based on loop areas. For example, in a cardiac pacemaker, there is a loop formed by the lead wire as it comes from the cardiac pacemaker housing to its distal TIP, for example, located in the right ventricle. The return path is through body fluid and tissue generally straight from the TIP electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 450 square centimeters).

Relating now to the specific case of MRI, the magnetic gradient fields would be induced through enclosed loop areas. However, the pulsed RF fields, which are generated by the body coil, would be primarily induced into the lead wire system by antenna action.

There are a number of potential problems with MRI, including: [0013] (1) Closure of the pacemaker reed switch. A pacemaker reed switch, which can also be a Hall Effect device, is designed to detect a permanent magnet held close to the patient's chest. This magnet placement allows a physician or even the patient to put the implantable medical device into what is known as the "magnet mode response." The "magnet mode response" varies from one manufacturer to another, however, in general, this puts the pacemaker into a fixed rate or asynchronous pacing mode. This is normally done for short times and is very useful for diagnostic and clinical purposes. However, in some cases, when a pacemaker is brought into the bore or close to the MRI scanner, the MRI static field can make the pacemaker's internal reed switch close, which puts the pacemaker into a fixed rate or asynchronous pacing mode. Worse yet, the reed switch may bounce or oscillate. Asynchronous pacing may compete with the patient's underlying cardiac rhythm. This is one reason why patients have generally been advised not to undergo MRI. Fixed rate or asynchronous pacing for most patients is not an issue. However, in patients with unstable conditions, such as myocardial ischemia, there is a substantial risk for ventricular fibrillation during asynchronous pacing. In most modern pacemakers the magnetic reed switch (or Hall Effect device) function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch. [0014] (2) Reed switch damage. Direct damage to the reed switch is theoretically possible, but has not been reported in any of the known literature. In an article written by Roger Christoph Luchinger of Zurich, he reports on testing in which reed switches were exposed to the static magnetic field of MRI equipment. After extended exposure to these static magnetic fields, the reed switches functioned normally at close to the same field strength as before the test. [0015] (3) Pacemaker displacement. Some parts of pacemakers, such as the batteries and reed switch, contain ferrous magnetic materials and are thus subject to mechanical forces during MRI. Pacemaker displacement may occur in response to magnetic force or magnetic torque. There are several recent reports on modern pacemakers and ICDs that force and torque are not of concern for MRI systems up to 3 Tesla. [0016] (4) Radio frequency field. At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Also, distal TIP design is very important as the distal TIP itself can act as its own antenna wherein eddy currents can create heating. The cause of heating in an MRI environment is two fold: (a) RF field coupling to the lead can occur which induces significant local heating; and (b) currents induced between the distal TIP and tissue during MRI RF pulse transmission sequences can cause local Ohms Law heating in tissue next to the distal TIP electrode of the implanted lead. The RF field of an MRI scanner can produce enough energy to induce lead wire currents sufficient to destroy some of the adjacent myocardial tissue. Tissue ablation has also been observed. The effects of this heating are not readily detectable by monitoring during the MRI. Indications that heating has occurred would include an increase in pacing threshold, venous ablation, Larynx or esophagal ablation, myocardial perforation and lead penetration, or even arrhythmias caused by scar tissue. Such long term heating effects of MRI have not been well studied yet for all types of AIMD lead wire geometries. There can also be localized heating problems associated with various types of electrodes in addition to TIP electrodes. This includes RING electrodes or PAD electrodes. RING electrodes are commonly used with a wide variety of implanted devices including cardiac pacemakers, neurostimulators, probes, catheters and the like. PAD electrodes are very common in neurostimulator applications. For example, spinal cord stimulators or deep brain stimulators can include a plurality of PAD electrodes to make contact with nerve tissue. A good example of this also occurs in a cochlear implant. In a typical cochlear implant there would be sixteen RING electrodes that the position places by pushing the electrode up into the cochlea. Several of these RING electrodes make contact with auditory nerves. [0017] (5) Alterations of pacing rate due to the applied radio frequency field. It has been observed that the RF field may induce undesirable fast pacing (QRS complex) rates. There are various mechanisms which have been proposed to explain rapid pacing: direct tissue stimulation, interference with pacemaker electronics or pacemaker reprogramming (or reset). In all of these cases, it is very desirable to raise the lead system impedance (at the MRI RF pulsed frequency) to make an EMI filter feedthrough capacitor more effective and thereby provide a higher degree of protection to AIMD electronics. This will make alterations in pacemaker pacing rate and/or pacemaker reprogramming much more unlikely. [0018] (6) Time-varying magnetic gradient fields. The contribution of the time-varying gradient to the total strength of the MRI magnetic field is negligible, however, pacemaker systems could be affected because these fields are rapidly applied and removed. The time rate of change of the magnetic field is directly related to how much electromagnetic force and hence current can be induced into a lead wire system. Luchinger reports that even using today's gradient systems with a time-varying field up to 50 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart. [0019] (7) Heating. Currents induced by time-varying magnetic gradient fields may lead to local heating. Researchers feel that the calculated heating effect of the gradient field is much less as compared to that caused by the RF field and therefore for the purposes herein may be neglected.

There are additional problems possible with implantable cardioverter defibrillators (ICDs). ICDs use different and larger batteries which could cause higher magnetic forces. The programmable sensitivity in ICDs is normally much higher (more sensitive) than it is for pacemakers, therefore, ICDs may falsely detect a ventricular tachyarrhythmia and inappropriately deliver therapy. In this case, therapy might include anti-tachycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. Fortunately, ICDs have a sort of built-in fail-safe mechanism. That is, during an MRI procedure, if they inadvertently sense the MRI fields as a dangerous ventricular arrhythmia, the ICD will attempt to charge up and deliver a high voltage shock. However, there is a transformer contained within the ICD that is necessary to function in order to charge up the high-energy storage capacitor contained within the ICD. In the presence of the main static field of the MRI the core of this transformer tends to saturate thereby preventing the high voltage capacitor from charging up. This makes it highly unlikely that an ICD patient undergoing an MRI would receive an inappropriate high voltage shock therapy. While ICDs cannot charge during MRI due to the saturation of their ferro-magnetic transformers, the battery will be effectively shorted and lose life. This is a highly undesirable condition.

In summary, there are a number of studies that have shown that MRI patients with active implantable medical devices, such as cardiac pacemakers, can be at risk for potential hazardous effects. However, there are a number of reports in the literature that MRI can be safe for imaging of pacemaker patients when a number of precautions are taken (only when an MRI is thought to be an absolute diagnostic necessity). These anecdotal reports are of interest, however, they are certainly not scientifically convincing that all MRI can be safe. As previously mentioned, just variations in the pacemaker lead wire length can significantly effect how much heat is generated. From the layman's point of view, this can be easily explained by observing the typical length of the antenna on a cellular telephone compared to the vertical rod antenna more common on older automobiles. The relatively short antenna on the cell phone is designed to efficiently couple with the very high frequency wavelengths (approximately 950 MHz) of cellular telephone signals. In a typical AM and FM radio in an automobile, these wavelength signals would not efficiently couple to the relatively short antenna of a cell phone. This is why the antenna on the automobile is relatively longer. An analogous situation exists with an AIMD patient in an MRI system. If one assumes, for example, a 3.0 Tesla MRI system, which would have an RF pulsed frequency of 128 MHz, there are certain implanted lead lengths that would couple efficiently as fractions of the 128 MHz wavelength. It is typical that a hospital will maintain an inventory of various leads and that the implanting physician will make a selection depending on the size of the patient, implant location and other factors. Accordingly, the implanted or effective lead wire length can vary considerably. There are certain implanted lead wire lengths that just do not couple efficiently with the MRI frequency and there are others that would couple very efficiently and thereby produce the worst case for heating.

The effect of an MRI system on the function of pacemakers, ICDs and neurostimulators depends on various factors, including the strength of the static magnetic field, the pulse sequence (gradient and RF field used), the anatomic region being imaged, and many other factors. Further complicating this is the fact that each patient's condition and physiology is different and each manufacturer's pacemaker and ICD designs also are designed and behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, the physician with patient informed consent may make the decision to perform MRI in spite of all of the previously described attendant risks to the pacemaker system.

Insulin drug pump systems do not seem to be of a major current concern due to the fact that they have no significant antenna components (such as implanted lead wires). However, some implantable pumps work on magneto-peristaltic systems, and must be deactivated prior to MRI. There are newer (unreleased) systems that would be based on solenoid systems which will have similar problems.

It is clear that MRI will continue to be used in patients with both external and active implantable medical devices. There are a number of other hospital procedures, including electro-cautery surgery, lithotripsy, etc., to which a pacemaker patient may also be exposed. Accordingly, there is a need for AIMD system and/or circuit protection devices which will improve the immunity of active implantable medical device systems to diagnostic procedures such as MRI.

As one can see, many of the undesirable effects in an implanted lead wire system from MRI and other medical diagnostic procedures are related to undesirable induced currents in the lead wire system and/or its distal TIP (or RING). This can lead to overheating either in the lead wire or at the body tissue at the distal TIP. For a pacemaker application, these currents can also directly stimulate the heart into sometimes dangerous arrhythmias.

Accordingly, there is a need for a novel resonant tank band stop filter assembly which can be placed at various locations along the active implantable medical device lead wire system, which also prevents current from circulating at selected frequencies of the medical therapeutic device. Preferably, such novel tank filters would be designed to resonate at 64 MHz for use in an MRI system operating at 1.5 Tesla (or 128 MHz for a 3 Tesla system). The present invention fulfills these needs and provides other related advantages.

SUMMARY OF THE INVENTION

An exemplary embodiment of the present invention includes an implantable lead configured to be permanently or removably connectable to an active implantable medical device. A lead conductor has a length extending from a proximal end to a distal end. An insulated and self-resonant inductive coil is connected in series along a portion of length of the lead conductor. The inductive coil comprises a parasitic capacitance between its adjacent turns such that the inductive coil becomes self-resonant at a selected center frequency or across a range of frequencies about the selected center frequency.

In other embodiments, the selected center frequency may include an MRI RF pulsed frequency. The insulated and self-resonant inductive coil may include a tank filter performance. The tank filter performance may attenuate the MRI RF pulsed frequency.

The self-resonant inductive coil may have an inductance with an associated resistance and a parasitic capacitance with an associated resistance which determines an overall Q of the tank filter performance. The overall Q of the tank filter performance may be on the order of megahertz. A resultant 3 dB bandwidth may be at least 128 kHz.

The tank filter performance may include less than or equal to 3 dB of attenuation for the biological frequency range of 0-1 kHz. Also, the tank filter performance may include greater than or equal to 15 dB of attenuation at or near the MRI RF pulsed frequency.

A dielectric coating may substantially surround the inductive coil. Furthermore, the insulated and self-resonant inductive coil may be shielded.

Another exemplary embodiment of the present invention includes an implantable lead configured to be permanently or removably connectable to an active implantable medical device. A lead conductor has a length extending from a proximal end to a distal end. A self-resonant inductor is connected in series along a portion of the length of the lead conductor. The self-resonant inductor includes a single length of conductive material comprising a dielectric coating substantially surrounding the single length of conductive material. The self-resonant inductor includes a first coiled or spiral conductor disposed along an inductor section spanning in a first direction from a first location to a second location. A second coiled or spiral conductor is disposed along the inductor section spanning in a second direction from the second location to the first location, wherein the second direction is opposite the first direction. A third coiled or spiral conductor is disposed along the inductor section spanning in the first direction from the first location to the second location.

In other embodiments, the first coiled or spiral conductor may be disposed within the second coiled or spiral conductor. The second coiled or spiral conductor may be disposed within the third coiled or spiral conductor.

The self-resonant inductor may include a parasitic capacitance between its adjacent turns wherein the inductor becomes self-resonant at a selected center frequency or across a range of frequencies about the selected center frequency. The selected center frequency may include an MRI RF pulsed frequency. The self-resonant inductor may include a tank filter performance. The tank filter performance may attenuate the MRI RF pulsed frequency.

The self-resonant inductive coil may have an inductance with an associated resistance and a parasitic capacitance with an associated resistance which determines an overall Q of the tank filter performance. The overall Q of the tank filter performance is on the order of megahertz.

A resultant 3 dB bandwidth may be at least 128 kHz. The tank filter performance may include less than or equal to 3 dB of attenuation for a biological frequency range of 0-1 kHz. The tank filter performance may include greater than or equal to 15 dB of attenuation at or near the MRI RF pulsed frequency. The self-resonant inductor may be shielded.

The single length of conductive material may include a cored, clad, plated, electroplated, anodized or filled tube construction. The single length of conductive material may include an inner conductive core substantially surrounded by an outer conductive layer. The outer conductive layer may be biocompatible. The outer conductive layer may include MP35N, nitinol, tungston, tantalum, niobium, Co—Cr—Mo alloys, stainless steel alloys, stainless steel alloys with Mo, Ni, Cr combinations, carbon steels, or any combination thereof. The inner conductive core may include silver, copper, platinum, platinum, platinum-iridium, platinum-tungsten, platinum alloys, tantalum, gold, palladium, nitinol, titanium or titanium alloys.

The dielectric coating may include a thermoset, thermoplastic or flexible coating. The thermoset dielectric coating may include a resin or modifier comprising pigments, plasticizers, filler particulates, flakes, spheres, nanoparticles, short fibers, long fibers, submicron fibers, isotropically dispersed submicron fibers, anistropically dispersed submicron fibers, laminate configurations or any combination thereof. The dielectric coating may include adhesives, elastomers, epoxies, fluoropolymers, copolymer blends, amorphous copolymer blends, semi-amorphous copolymer blends, copolymer blends with limited crosslinking or any combination thereof. The dielectric coating may include acrylonitrile butadiene styrene (ABS), acrylics, poly(methyl methacrylate) or PMMA, celluloids, acetates, cellulose acetate, ethylene-vinyl acetate, copolymers, cyclic olefin copolymer, polyethylene, poly(vinyl chloride), polystyrene, acetals, urethanes, carbothane, estane, pellethane, Tecoflex, Tecothane, Texin, nylons, Aesno, Besno, Nylon 6, Nylon 6,6, Nylon 12, Pebax, Vestamid, polyether, polyester, polypropylene, polytetrafluoroethylene (PTFE), FEP, PFA, CTFE, ECTFE, PEEK, ETFE, PET, PBT, polyvinylidine fluoride (PVDF), ETTFE, THV, polycarbonate, polyetherimide, polysulfone, parylene, polyethelene, polypropylene, polyether block amids (PEBAX), acid copolymers, or any combination thereof.

Another exemplary embodiment of the present invention includes an implantable lead configured to be permanently or removably connectable to an active implantable medical device. A lead conductor has a length extending from a proximal end to a distal end. A self-resonant inductor is connected in series along a portion of the length of the lead conductor. The self-resonant inductor includes a first coiled or spiral conductor disposed along an inductor section spanning in a first direction from a first location to a second location. A second coiled or spiral conductor is disposed along the inductor section spanning in a second direction from the second location to the first location, wherein the second direction is opposite the first direction. A third coiled or spiral conductor is disposed along the inductor section spanning in the first direction from the first location to the second location.

In other embodiments, the first coiled or spiral conductor may be electrically connected to the second coiled or spiral conductor. The second coiled or spiral conductor may be electrically connected to the third coiled or spiral conductor.

The first coiled or spiral conductor may be disposed within the second coiled or spiral conductor. The second coiled or spiral conductor may be disposed within the third coiled or spiral conductor.

The first, second and third coiled or spiral conductors may include a dielectric coating substantially surrounding the conductors.

The first, second and third coiled or spiral conductors may include a continuous single length of conductive material.

The self-resonant inductor may include a parasitic capacitance between its adjacent turns between the first and second coiled or spiral conductors and the second and third coiled or spiral conductors wherein the inductor becomes self-resonant at a selected center frequency or across a range of frequencies about the selected center frequency. The selected center frequency may include an MRI RF pulsed frequency.

The self-resonant inductor may include a tank filter performance attenuating the MRI RF pulsed frequency. The tank filter performance may include less than or equal to 3 dB of attenuation for a biological frequency range of 0-1 kHz. The tank filter performance may include greater than or equal to 15 dB of attenuation at or near the MRI RF pulsed frequency. A resultant 3 dB bandwidth may be at least 128 kHz. The self-resonant inductor may be shielded.

Another exemplary embodiment of the present invention includes an implantable lead configured to be permanently or removably connectable to an active implantable medical device. A lead conductor has a length extending from a proximal end to a distal end. A self-resonant inductor is connected in series along a portion of the length of the lead conductor. The self-resonant inductor includes a single length of conductive material including a dielectric coating substantially surrounding the single length of conductive material. The self-resonant inductor includes a first coiled or spiral conductor disposed along an inductor section spanning in a first direction from a first location to a second location. A second coiled or spiral conductor is disposed along the inductor section spanning in a second direction from the second location to the first location, where the second direction is opposite the first direction. A third conductor is disposed along the inductor section spanning in the first direction from the first location to the second location.

In other embodiments, the third conductor may be disposed inside or outside both the first and second coiled or spiral conductors.

The self-resonant inductor may include a parasitic capacitance between its adjacent turns wherein the inductor becomes self-resonant at a selected center frequency or across a range of frequencies about the selected center frequency. The selected center frequency may include an MRI RF pulsed frequency and the self-resonant inductor may include a tank filter performance attenuating the MRI RF pulsed frequency. The tank filter performance may include less than or equal to 3 dB of attenuation for a biological frequency range of 0-1 kHz. The tank filter performance may include greater than or equal to 15 dB of attenuation at or near the MRI RF pulsed frequency. A resultant 3 dB bandwidth is at least 128 kHz.

Another exemplary embodiment of the present invention includes an implantable lead configured to be permanently or removably connectable to an active implantable medical device. A lead conductor has a length extending from a proximal end to a distal end. A self-resonant inductor is connected in series along a portion of the length of the lead conductor. The self-resonant inductor includes a single length of conductive material including a dielectric coating substantially surrounding the single length of conductive material. The self-resonant inductor includes a first coiled or spiral conductor disposed along an inductor section spanning in a first direction from a first location to a second location. A second conductor is disposed along the inductor section in a second direction opposite the first direction spanning from the second location to the first location. A third coiled or spiral conductor is disposed along the inductor section spanning in the first direction from the first location to the second location.

In other embodiments, the first coiled or spiral conductor may be disposed inside the third coiled or spiral conductor, and wherein the second conductor may be disposed between the first and second coiled or spiral conductors. The self-resonant inductor may include a parasitic capacitance between its adjacent turns wherein the inductor becomes self-resonant at a selected center frequency or across a range of frequencies about the selected center frequency.

The selected center frequency may include an MRI RF pulsed frequency and the self-resonant inductor may include a tank filter performance attenuating the MRI RF pulsed frequency.

The tank filter performance may include less than or equal to 3 dB of attenuation for a biological frequency range of 0-1 kHz. The tank filter performance may include greater than or equal to 15 dB of attenuation at or near the MRI RF pulsed frequency. A resultant 3 dB bandwidth may be at least 128 kHz.

Another exemplary embodiment of the present includes an RF/MRI compatible medical device. The medical device includes an elongate electrical medical lead having at least one conductor with opposing proximal and distal portions. The at least one conductor has a first section that extends in a first lengthwise direction for a first physical length, then turns to define at least one reverse section that extends in a substantially opposing lengthwise direction for a second physical length, then turns again to define a third section that extends in the first lengthwise direction for a third physical length.

In other embodiments, at least one of the sections has a coiled portion. In another embodiment, at least two of the sections have a coiled portion. In another embodiment, at least one of the first, reverse or third sections extends under, over or through a neighboring section. In another embodiment, at least one of the sections resides proximate to and outside of a coiled portion of another section. In another embodiment, the first, reverse and third sections may include a continuous single length of conductive material. In another embodiment, the first, reverse and third sections may include a dielectric coating.

Another exemplary embodiment of the present invention includes an implantable lead configured to be permanently or removably connectable to an active implantable medical device. A lead conductor has a length extending from a proximal end to a distal end. A self-resonant inductor is connected in series along a portion of the length of the lead conductor. The self-resonant inductor includes a single length of conductive material comprising a dielectric coating substantially surrounding the single length of conductive material. The self-resonant inductor includes an n number of insulated coiled or spiral conductors disposed along an inductor section spanning back and forth between a first location and a second location, where the n number comprises two or more even number of insulated coiled or spiral conductors. A return conductor is electrically connected to the n number of coiled or spiral conductors.

Another exemplary embodiment of the present invention includes an implantable lead configured to be permanently or removably connectable to an active implantable medical device. A lead conductor has a length extending from a proximal end to a distal end. A self-resonant inductor is connected in series along a portion of the length of the lead conductor. The self-resonant inductor includes a single length of conductive material comprising a dielectric coating substantially surrounding the single length of conductive material. The self-resonant inductor includes an n number of insulated coiled or spiral conductors disposed along an inductor section spanning back and forth between a first location and a second location, wherein the n number comprises three or more odd number of insulated coiled or spiral conductors.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 12 is a chart illustrating calculation of frequency of resonance for the parallel tank circuit of FIG. 11;

FIG. 14 is an equation for the impedance of an inductor in parallel with a capacitor;

FIG. 15 is a chart illustrating reactance equations for the inductor and the capacitor of the parallel tank circuit of FIG. 11;

DETAILED DESCRIPTION OF THE PREFERRED EMBODIMENTS

Figure 1:
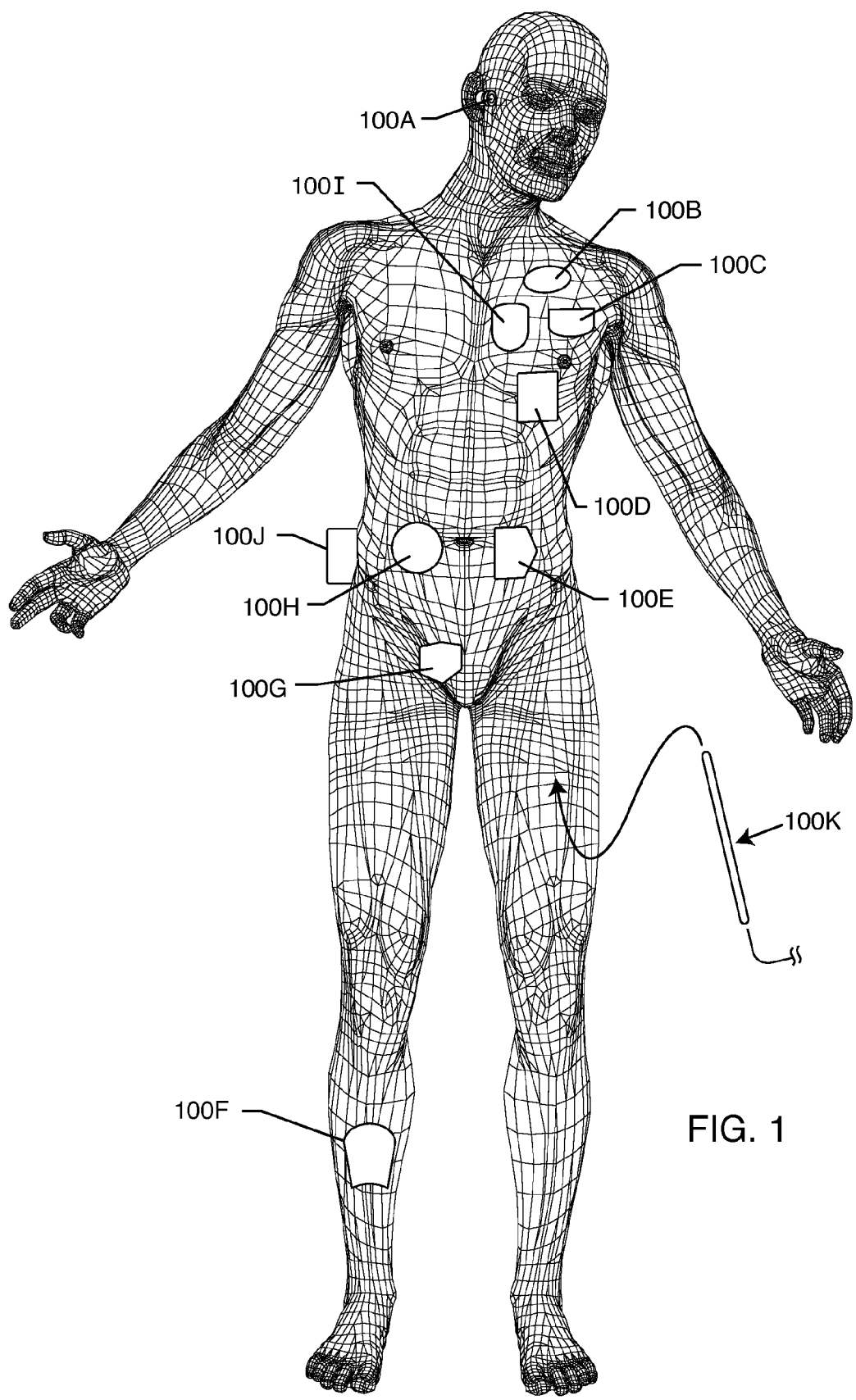
FIG. 1 is a wire-formed diagram of a generic human body showing a number of active implantable medical devices (AIMDs)

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise knows as CRT devices. 100J illustrates an externally worn pack. This pack could be an external insulin pump, an external drug pump, an external neurostimulator, a Holter monitor with skin electrodes or even a ventricular assist device power pack. 100K illustrates the insertion of an external probe or catheter. These probes can be inserted into the femoral artery, for example, or in any other number of locations in the human body.

Figure 2:
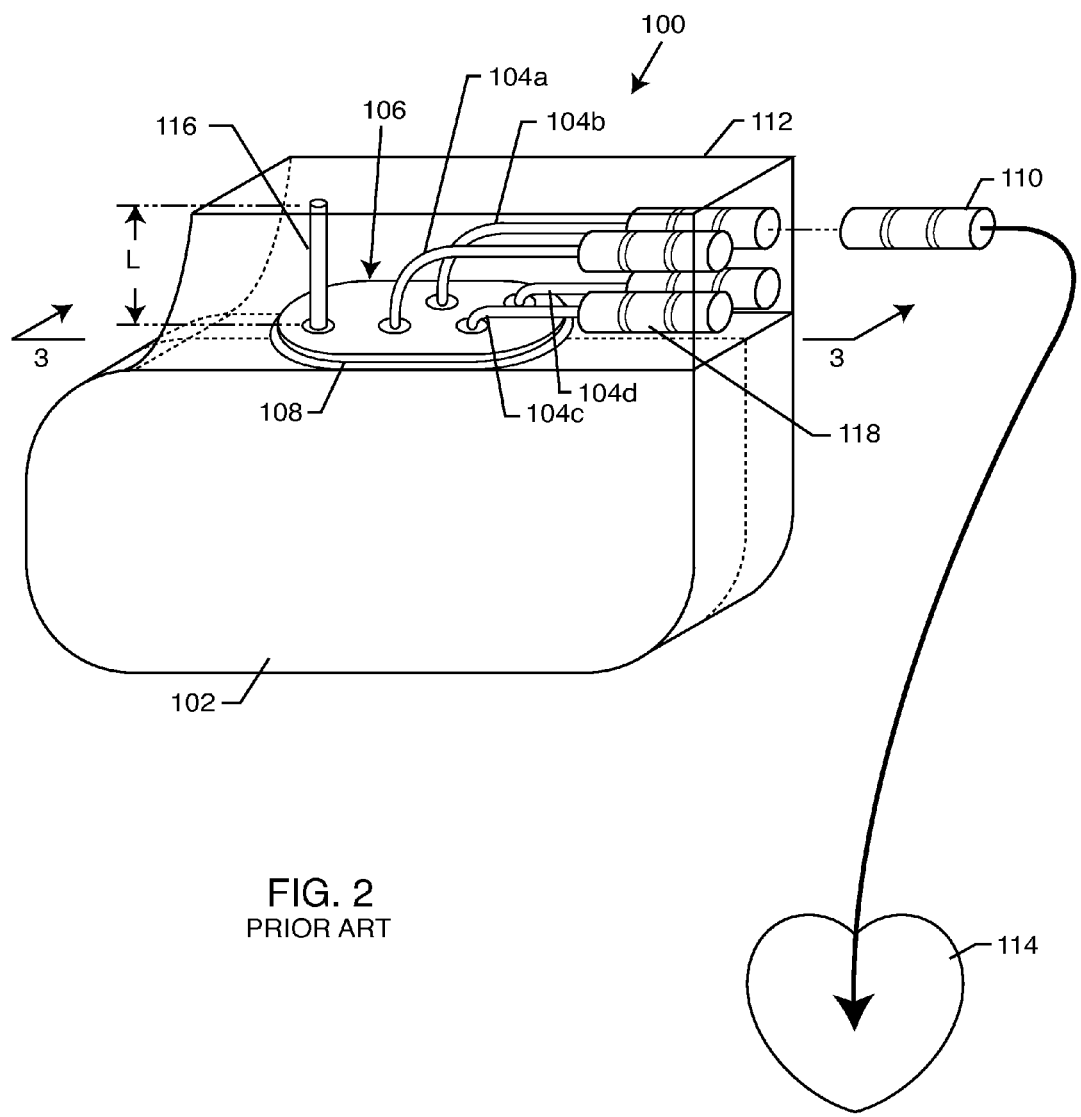
FIG. 2 is a perspective and somewhat schematic view of a prior art active implantable medical device (AIMD) including a lead wire directed to the heart of a patient.

Referring now to FIG. 2, a prior art active implantable medical device (AIMD) 100 is illustrated. In general, the AIMD 100 could, for example, be a cardiac pacemaker 100C which is enclosed by a titanium housing 102 as indicated. The titanium housing is hermetically sealed, however there is a point where lead wires 104 must ingress and egress the hermetic seal. This is accomplished by providing a hermetic terminal assembly 106. Hermetic terminal assemblies are well known and generally consist of a ferrule 108 which is laser welded to the titanium housing 102 of the AIMD 100. The hermetic terminal assembly 106 with its associated EMI filter is better shown in FIG. 3. Referring once again to FIG. 2, four lead wires are shown consisting of lead wire pair 104a and 104b and lead wire pair 104c and 104d. This is typical of what's known as a dual chamber bipolar cardiac pacemaker.

The IS1 connectors 110 that are designed to plug into the header block 112 are low voltage (pacemaker) connectors covered by an ANSI/AAMI standard IS-1. Higher voltage devices, such as implantable cardioverter defibrillators, are covered by a standard known as the ANSI/AAMI DF-1. There is a new standard under development which will integrate both high voltage and low voltage connectors into a new miniature connector series known as the IS-4 series. These connectors are typically routed in a pacemaker application down into the right ventricle and right atrium of the heart 114. There are also new generation devices that have been introduced to the market that couple lead wires to the outside of the left ventricle. These are known as biventricular devices and are very effective in cardiac resynchronization therapy (CRT) and treating congestive heart failure (CHF).

Referring once again to FIG. 2, one can see, for example, the bipolar lead wires 104a and 104b that could be routed, for example, to the distal TIP and RING into the right ventricle. The bipolar lead wires 104c and 104d could be routed to a distal TIP and RING in the right atrium. There is also an RF telemetry pin antenna 116 which is not connected to the IS-1 or DS-1 connector block. This acts as a short stub antenna for picking up telemetry signals that are transmitted from the outside of the device 100.

It should also be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as an ICD. Ventricular assist devices also can fall into this type of category. This list is not meant to be limiting, but is only example of the applications of the novel technology currently described herein.

Figure 3:
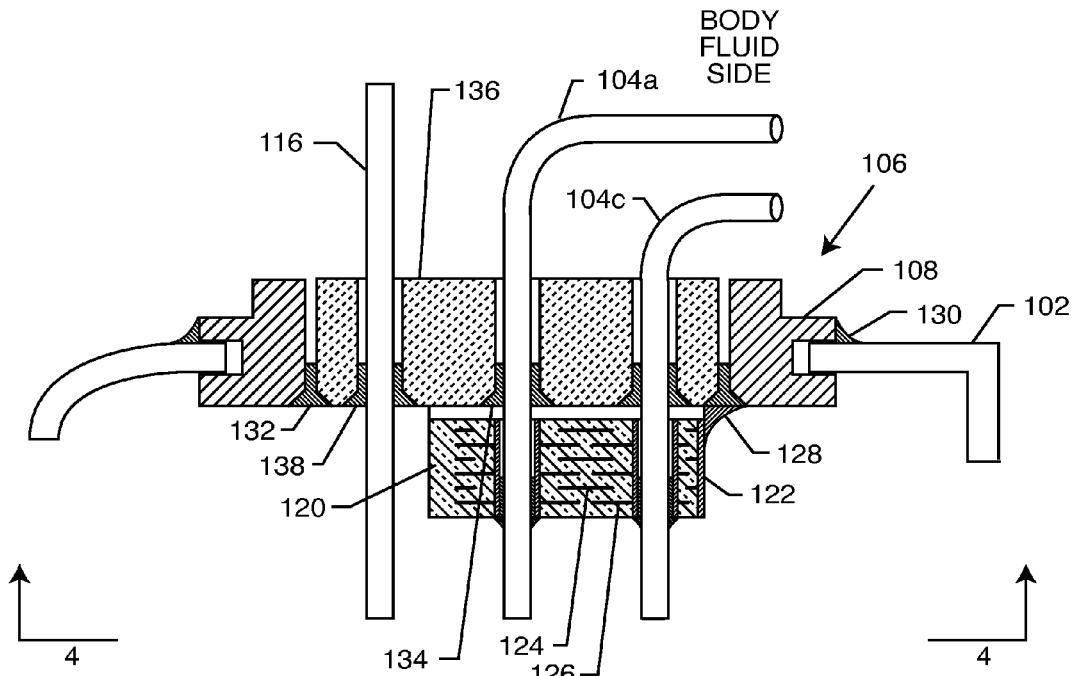
FIG. 3 is an enlarged sectional view taken generally along the line 3-3 of FIG. 2.

FIG. 3 is an enlarged, fragmented cross-sectional view taken generally along line 3-3 of FIG. 2. Here one can see in cross-section the RF telemetry pin 116 and the bipolar lead wires 104a and 104c which would be routed to the cardiac chambers by connecting these lead wires to the internal connectors 118 of the IS-1 header block 112 (FIG. 2). These connectors are designed to receive the plug 110 which allows the physicians to thread lead wires through the venous system down into the appropriate chambers of the heart 114. It will be obvious to those skilled in the art that tunneling of deep brain electrodes or neurostimulators are equivalent.

Referring back to FIG. 3, one can see a prior art feedthrough capacitor 120 which has been bonded to the hermetic terminal assembly 106. These feedthrough capacitors are well known in the art and are described and illustrated in U.S. Pat. Nos. 5,333,095, 5,751,539, 5,978,204, 5,905,627, 5,959,829, 5,973,906, 5,978,204, 6,008,980, 6,159,560, 6,275,369, 6,424,234, 6,456,481, 6,473,291, 6,529,103, 6,566,978, 6,567,259, 6,643,903, 6,675,779, 6,765,780 and 6,882,248. In this case, a rectangular quadpolar feedthrough capacitor 120 is illustrated which has an external metalized termination surface 122. It includes embedded electrode plate sets 124 and 126. Electrode plate set 124 is known as the ground electrode plate set and is terminated at the outside of the capacitor 120 at the termination surface 122. These ground electrode plates 124 are electrically and mechanically connected to the ferrule 108 of the hermetic terminal assembly 106 using a thermosetting conductive polyimide or equivalent material 128 (equivalent materials will include solders, brazes, conductive epoxies and the like). In turn, the hermetic seal terminal assembly 106 is designed to have its titanium ferrule 108 laser welded 130 to the overall housing 102 of the AIMD 100. This forms a continuous hermetic seal thereby preventing body fluids from penetrating into and causing damage to the electronics of the AIMD.

It is also essential that the lead wires 104 and insulator 136 be hermetically sealed, such as by the gold brazes or glass seals 132 and 134. The gold braze 132 wets from the titanium ferrule 108 to the alumina ceramic insulator 136. In turn, the ceramic alumina insulator 136 is also gold brazed at 134 to each of the lead wires 104. The RF telemetry pin 116 is also gold brazed at 138 to the alumina ceramic insulator 136. It will be obvious to those skilled in the art that there are a variety of other ways of making such a hermetic terminal. This would include glass sealing the leads into the ferrule directly without the need for the gold brazes.

As shown in FIG. 3, the RF telemetry pin 116 has not been included in the area of the feedthrough capacitor 120. The reason for this is the feedthrough capacitor 120 is a very broadband single element EMI filter which would eliminate the desirable telemetry frequency.

Figure 4:
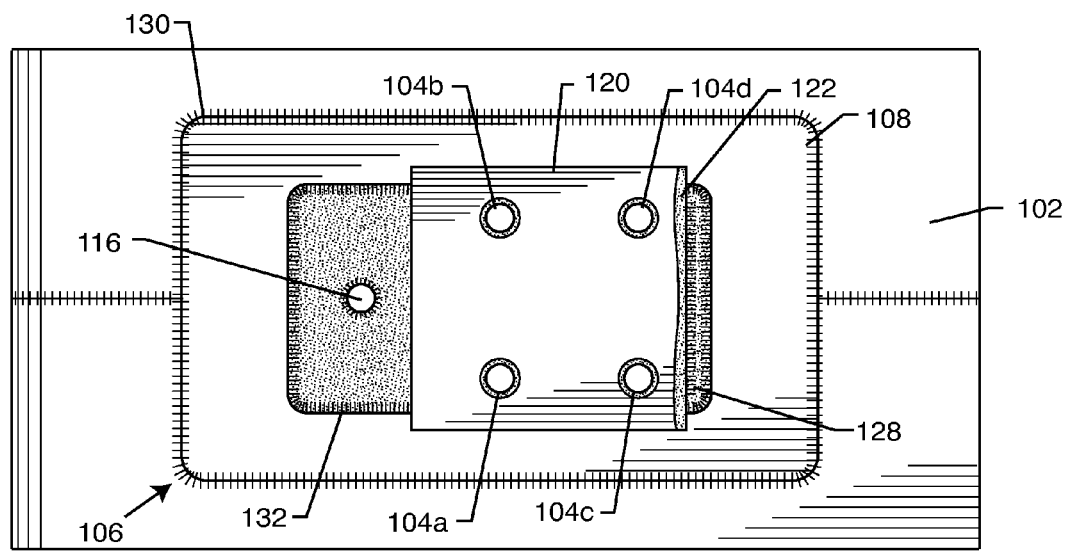
FIG. 4 is a view taken generally along the line 4-4 of FIG. 3.

FIG. 4 is a bottom view taken generally along line 4-4 in FIG. 3. One can see the gold braze 132 which completely seals the hermetic terminal insulator 136 into the overall titanium ferrule 108. One can also see the overlap of the capacitor attachment materials, shown as a thermosetting conductive adhesive 128, which makes contact to the gold braze 132 that forms the hermetic terminal 106.

Figure 5:
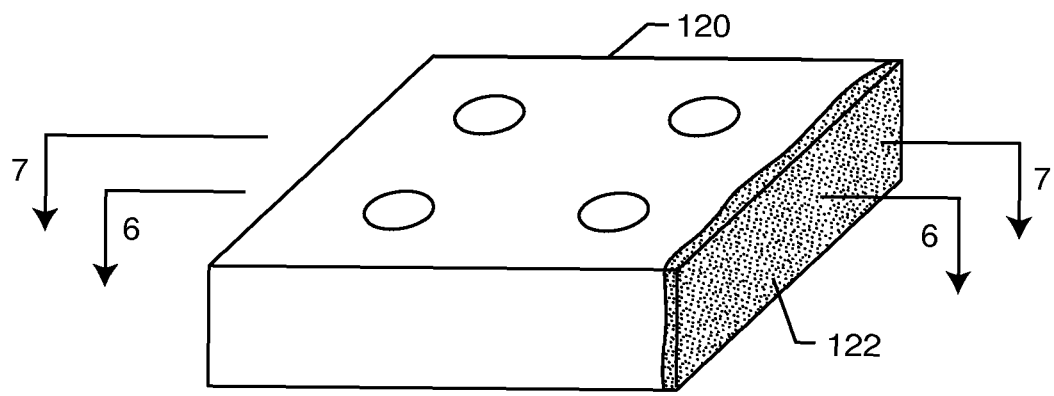
FIG. 5 is a perspective/isometric view of a prior art rectangular quadpolar feedthrough capacitor of the type shown in FIGS. 3 and 4.
Figure 6:
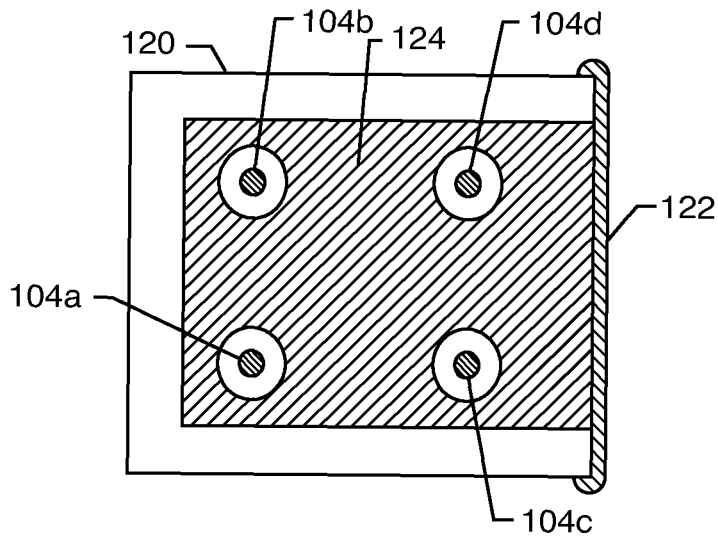
FIG. 6 is sectional view taken generally along the line 6-6 of FIG. 5.
Figure 7:
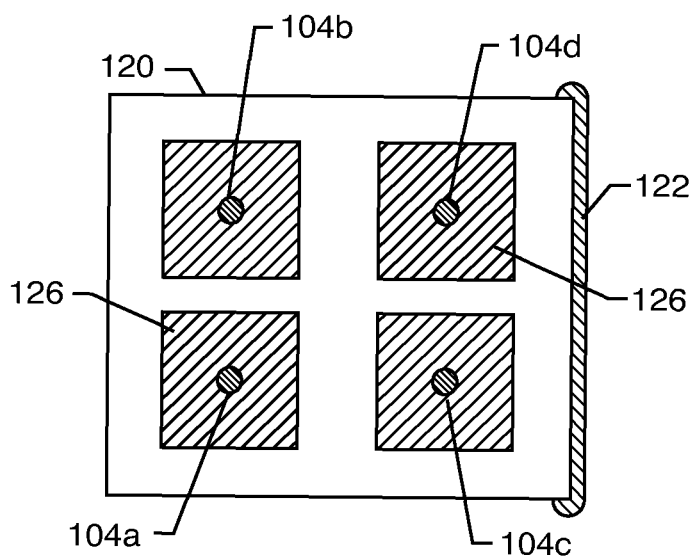
FIG. 7 is a sectional view taken generally along the line 7-7 of FIG. 5.

FIG. 5 is an isometric view of the feedthrough capacitor 120. As one can see, the termination surface 122 connects to the capacitor's internal ground plate set 124. This is best seen in FIG. 6 where ground plate set 124, which is typically silk-screened onto ceramic layers, is brought out and exposed to the termination surface 122. The capacitor's four (quadpolar) active electrode plate sets 126 are illustrated in FIG. 7. In FIG. 6 one can see that the lead wires 104 are in non-electrical communication with the ground electrode plate set 124. However, in FIG. 7 one can see that each one of the lead wires 104 is in electrical contact with its corresponding active electrode plate set 126. The amount of capacitance is determined by the overlap of the active electrode plate area 126 over the ground electrode plate area. One can increase the amount of capacitance by increasing the area of the active electrode plate set 126. One can also increase the capacitance by adding additional layers. In this particular application, we are only showing six electrode layers: three ground plates 124 and three active electrode plate sets 126 (FIG. 3). However, 10, 60 or even more than 100 such sets can be placed in parallel thereby greatly increasing the capacitance value. The capacitance value is also related to the dielectric thickness or spacing between the ground electrode set 124 and the active electrode set 126. Reducing the dielectric thickness increases the capacitance significantly while at the same time reducing its voltage rating. This gives the designer many degrees of freedom in selecting the capacitance value.

In the following description, functionally equivalent elements shown in various embodiments will often be referred to utilizing the same reference number.

Figure 8:
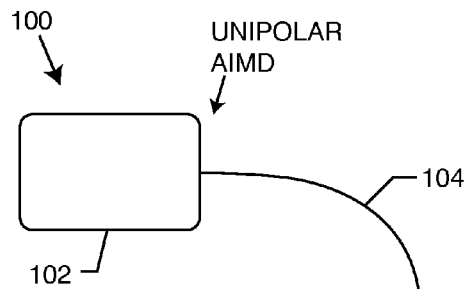
FIG. 8 is a diagram of a unipolar active implantable medical device.

FIG. 8 is a general diagram of a unipolar active implantable medical device system 100. FIG. 8 could also be representative of an externally worn medical device such as a Holter monitor. In the case of a Holter monitor, the distal electrode 140 would typically be a scan or patch electrode. The housing 102 of the active implantable medical device 100 is typically titanium, ceramic, stainless steel or the like. Inside of the device housing are the AIMD electronic circuits. Usually AIMDs include a battery, but that is not always the case. For example, for a Bion, it can receive its energy from an external pulsing magnetic field. A lead wire 104 is routed from the AIMD 100 to a point 140 where it is embedded in or affixed to body tissue. In the case of a spinal cord stimulator 100H, the distal TIP 140 could be in the spinal cord. In the case of a deep brain stimulator 100B, the distal electrode 140 would be placed deep into the brain, etc. In the case of a cardiac pacemaker 100C, the distal electrode 140 would typically be placed in the cardiac right ventricle.

Figure 9:
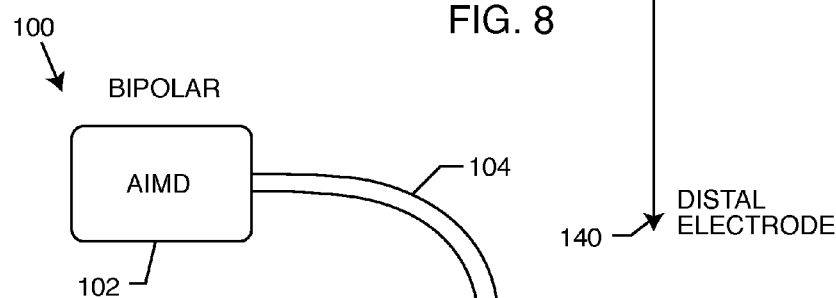
FIG. 9 is a diagram similar to FIG. 8, illustrating a bipolar AIMD system.

FIG. 9 is very similar to FIG. 8 except that it is a bipolar system. In this case, the electric circuit return path is between the two distal electrodes 140 and 140'. In the case of a cardiac pacemaker 100C, this would be known as a bipolar lead wire system with one of the electrodes known as the distal TIP 142 and the other electrode which would float in the blood pool known as the RING 144 (see FIG. 10). In contrast, the electrical return path in FIG. 8 is between the distal electrode 140 through body tissue to the conductive housing 102 of the implantable medical device 100.

Figure 10:
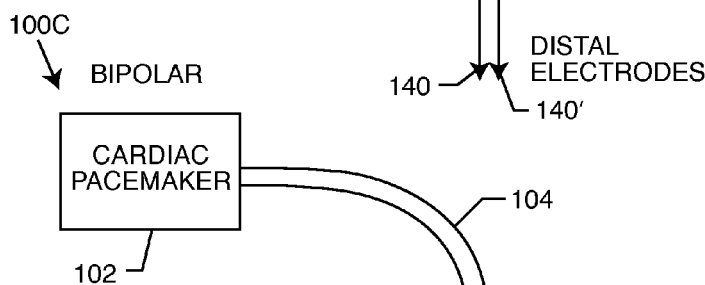
FIG. 10 is a diagram similar to FIGS. 8 and 9, illustrating a bipolar lead wire system with a distal TIP and RING, typically used in a cardiac pacemaker.

FIG. 10 illustrates a bipolar lead wire system with a distal TIP 142 and RING 144 typically as used in a cardiac pacemaker 100C. In all of these applications, the patient could be exposed to the fields of an MRI scanner or other powerful emitter used during a medical diagnostic procedure. Currents that are directly induced in the lead wire system 104 can cause heating by $I^2R$ losses in the lead wire system or by heating caused by current flowing in body tissue. If these currents become excessive, the associated heating can cause damage or even destructive ablation to body tissue.

The distal TIP 142 is designed to be implanted into or affixed to the actual myocardial tissue of the heart. The RING 144 is designed to float in the blood pool. Because the blood is flowing and is thermally conductive, the RING 144 structure is substantially cooled. In theory, however, if the lead curves, the RING 144 could also touch and become encapsulated by body tissue. The distal TIP 142, on the other hand, is always thermally insulated by surrounding body tissue and can readily heat up due to the RF pulse currents of an MRI field.

Figure 11:
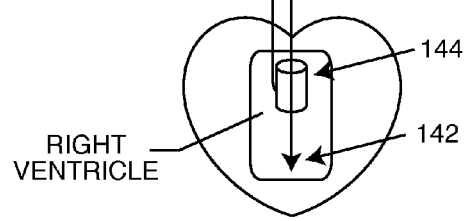
FIG. 11 is a schematic diagram showing a parallel combination of an inductor L and a capacitor C placed in series with the lead wire systems of FIGS. 8-10.

FIG. 11 is a schematic diagram showing a parallel combination of an inductor L and a capacitor C to be placed in the lead wire systems 104 previously described. This combination forms a parallel tank circuit or band stop filter 146 which will resonate at a particular frequency ($f_r$).

FIG. 12 gives the frequency of resonance equation $f_r$ for the parallel tank circuit 146 of FIG. 11: where $f_r$ is the frequency of resonance in hertz, L is the inductance in henries and C is the capacitance in farads. MRI systems vary in static field strength from 0.5 Tesla all the way up to 3 Tesla with newer research machines going much higher. This is the force of the main static magnetic field. The frequency of the pulsed RF field associated with MRI is found by multiplying the static field in Teslas times 42.45. Accordingly, a 3 Tesla MRI system has a pulsed RF field of approximately 128 MHz.

Referring once again to FIG. 11, one can see that if the values of the inductor and the capacitor are selected properly, one could obtain a parallel tank resonant frequency of 128 MHz. For a 1.5 Tesla MRI system, the RF pulse frequency is 64 MHz. Referring to FIG. 12, one can see the calculations assuming that the inductor value L is equal to one nanohenry. The one nanohenry comes from the fact that given the small geometries involved inside of the human body, a very large inductor will not be possible. This is in addition to the fact that the use of ferrite materials or iron cores for such an inductor are not practical for two reasons: 1) the static magnetic field from the MRI scanner would align the magnetic dipoles (saturate) in such a ferrite and therefore make the inductor ineffective; and 2) the presence of ferrite materials will cause severe MRI image artifacts. What this means is that if one were imaging the right ventricle of the heart, for example, a fairly large area of the image would be blacked out or image distorted due to the presence of these ferrite materials and the way it interacts with the MRI field. It is also important that the inductance value not vary while in the presence of the main static field.

The relationship between the parallel inductor L and capacitor C is also very important. One could use, for example, a very large value of inductance which would result in a very small value of capacitance to be resonant, for example, at the MRI frequency of 64 MHz. However, using a very high value of inductor results in a high number of turns of very small wire. Using a high number of turns of very small diameter wire is contraindicated for two reasons. The first reason is that the long length of relatively small diameter wire results in a very high DC resistance for the inductor. This resistance is very undesirable because low frequency pacing or neurostimulator pulses would lose energy passing through the relatively high series resistance. This is also undesirable where the AIMD is sensing biologic signals. For example, in the case of a pacemaker or deep brain stimulator, continuous sensing of low frequency biological signals is required. Too much series resistance in a lead wire system will attenuate such signals thereby making the AIMD less efficient. Accordingly, it is a preferred feature of the present invention that a relatively large value of capacitance will be used in parallel with a relatively small value of inductance, for example, employing highly volumetrically efficient ceramic dielectric capacitors that can create a great deal of capacitance in a very small space.

It should be also noted that below resonance, particularly at very low frequencies, the current in the parallel L-C band width stop filter passes through the inductor element. Accordingly, it is important that the parasitic resistance of the inductor element be quite low. Conversely, at very low frequencies, no current passes through the capacitor element. At high frequencies, the reactance of the capacitor element drops to a very low value. However, as there is no case where it is actually desirable to have high frequencies pass through the tank filter, the parasitic resistive loss of the capacitor is not particularly important. This is also known as the capacitor's equivalent series resistance (ESR). A component of capacitor ESR is the dissipation factor of the capacitor (a low frequency phenomenon). Off of resonance, it is not particularly important how high the capacitor's dissipation factor or overall ESR is when used as a component of a parallel tank circuit 146 as described herein. Accordingly, an air wound inductor is the ideal choice because it is not affected by MRI signals or fields. Because of the space limitations, however, the inductor will not be very volumetrically efficient. For this reason, it is preferable to keep the inductance value relatively low (in the order of 1 to 100 nanohenries).

Referring once again to FIG. 12, one can see the calculations for capacitance by algebraically solving the resonant frequency $f_r$ equation shown for C. Assuming an inductance value of one nanohenry, one can see that 6 nano-farads of capacitance would be required. Six nano-farads of capacitance is a relatively high value of capacitance. However, ceramic dielectrics that provide a very high dielectric constant are well known in the art and are very volumetrically efficient. They can also be made of biocompatible materials making them an ideal choice for use in the present invention.

Figure 13:
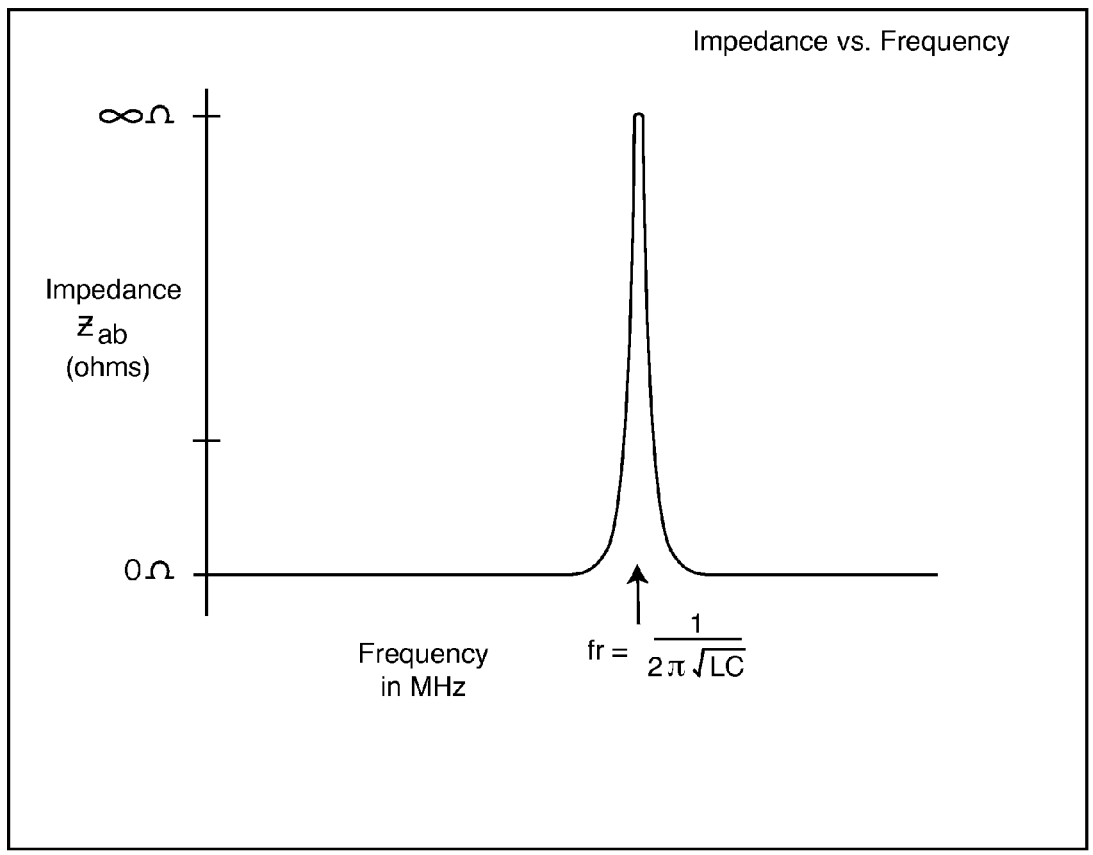
FIG. 13 is a graph showing impedance versus frequency for the parallel tank band stop circuit of FIG. 11.

FIG. 13 is a graph showing impedance versus frequency for the parallel tank, band stop filter circuit 146 of FIG. 11. As one can see, using ideal circuit components, the impedance measured between points A and B for the parallel tank circuit 146 shown in FIG. 11 is very low (zero) until one approaches the resonant frequency $f_r$. At the frequency of resonance, these ideal components combine together to look like a very high or, ideally, an infinite impedance. The reason for this comes from the denominator of the equation $Z_{ab}$ for the impedance for the inductor in parallel with the capacitor shown as FIG. 14. When the inductive reactance is equal to the capacitive reactance, the two imaginary vectors cancel each other and go to zero. Referring to the equations in FIGS. 14 and 15, one can see in the impedance equation for $Z_{ab}$, that a zero will appear in the denominator when $X_L=X_C$. This has the effect of making the impedance approach infinity as the denominator approaches zero. As a practical matter, one does not really achieve an infinite impedance. However, tests have shown that several hundred ohms can be realized which offers a great deal of attenuation and protection to RF pulsed currents from MRI. What this means is that at one particular unique frequency, the impedance between points A and B in FIG. 11 will appear very high (analogous to opening a switch). Accordingly, it would be possible, for example, in the case of a cardiac pacemaker, to design the cardiac pacemaker for compatibility with one single popular MRI system. For example, in the AIMD patient literature and physician manual it could be noted that the pacemaker lead wire system has been designed to be compatible with 3 Tesla MRI systems. Accordingly, with this particular device, a distal TIP band stop filter 146 would be incorporated where the L and the C values have been carefully selected to be resonant at 128 MHz, presenting a high or almost infinite impedance at the MRI pulse frequency.

Figure 16:
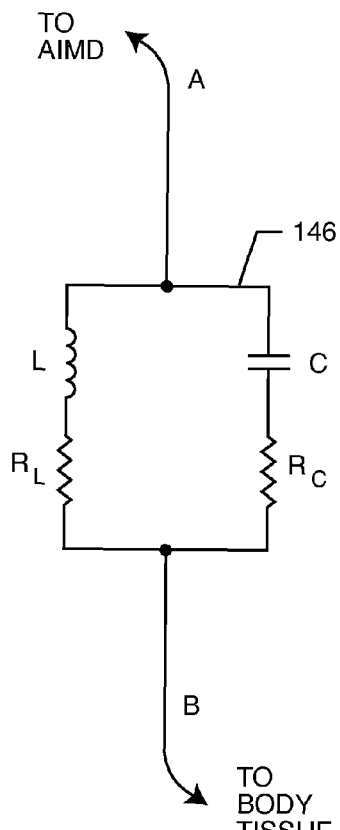
FIG. 16 is a schematic diagram illustrating the parallel tank circuit of FIG. 1, except in this case the inductor and the capacitor have series resistive losses.

FIG. 16 is a schematic drawing of the parallel tank circuit 146 of FIG. 11, except in this case the inductor L and the capacitor C are not ideal. That is, the capacitor C has its own internal resistance $R_C$, which is otherwise known in the industry as dissipation factor or equivalent series resistance (ESR). The inductor L also has a resistance $R_L$. For those that are experienced in passive components, one would realize that the inductor L would also have some parallel capacitance. This parasitic capacitance comes from the capacitance associated with adjacent turns. However, the inductance value contemplated is so low that one can assume that at MRI pulse frequencies, the inductor's parallel capacitance is negligible. One could also state that the capacitor C also has some internal inductance which would appear in series. However, the novel capacitors described below are very small or coaxial and have negligible series inductance. Accordingly, the circuit shown in FIG. 16 is a very good approximation model for the novel parallel tank circuits 146 as described herein.

This is best understood by looking at the FIG. 16 circuit 146 at the frequency extremes. At very low frequency, the inductor reactance equation is $X_L=2*pi*fL$ (reference FIG. 15). When the frequency f is close to zero (DC), this means that the inductor looks like a short circuit. It is generally the case that biologic signals are low frequency, typically between 10 Hz and 1000 Hz. For example, in a cardiac pacemaker 100C, all of the frequencies of interest appear between 10 Hz and 1000 Hz. At these low frequencies, the inductive reactance $X_L$ will be very close to zero ohms. Over this range, on the other hand, the capacitive reactance $X_C$ which has the equation $X_C=1/(2*pi*fc)$ will look like an infinite or open circuit (reference FIG. 15). As such, at low frequencies, the impedance between points A and B in FIG. 16 will equal to $R_L$. Accordingly, the resistance of the inductor ($R_L$) should be kept as small as possible to minimize attenuation of biologic signals or attenuation of stimulation pulses to body tissues. This will allow biologic signals to pass through the band stop filter 146 freely. It also indicates that the amount of capacitive loss $R_C$ is not particularly important. As a matter of fact, it would be desirable if that loss were fairly high so as to not freely pass very high frequency signals (such as undesirable EMI from cellular phones). It is also desirable to have the Q of the circuit shown in FIG. 16 relatively low so that the band stop frequency bandwidth can be a little wider. In other words, in a preferred embodiment, it would be possible to have a band stop wide enough to block both 64 MHz and 128 MHz frequencies thereby making the medical device compatible for use in both 1.5 Tesla and 3 Tesla MRI systems.

Figure 17:
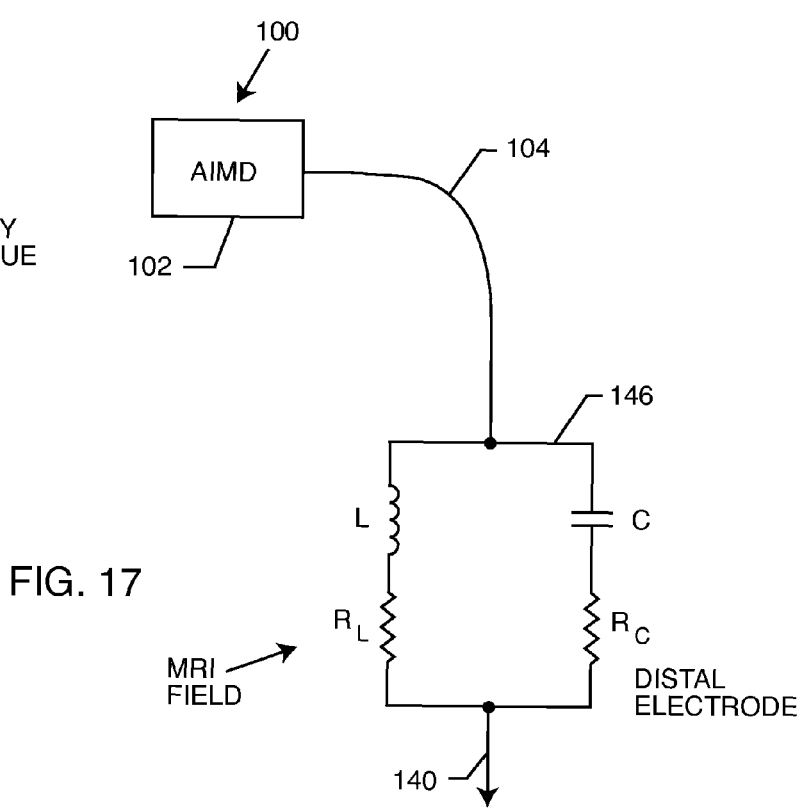
FIG. 17 is a diagram similar to FIG. 8, illustrating the tank circuit/band stop filter added near a distal electrode.

FIG. 17 is a drawing of the unipolar AIMD lead wire system, previously shown in FIG. 8, with the band stop filter 146 of the present invention added near the distal electrode 140. As previously described, the presence of the tank circuit 146 will present a very high impedance at one or more specific MRI RF pulse frequencies. This will prevent currents from circulating through the distal electrode 140 into body tissue at this selected frequency(s). This will provide a very high degree of important protection to the patient so that overheating does not cause tissue damage.

Figure 18:
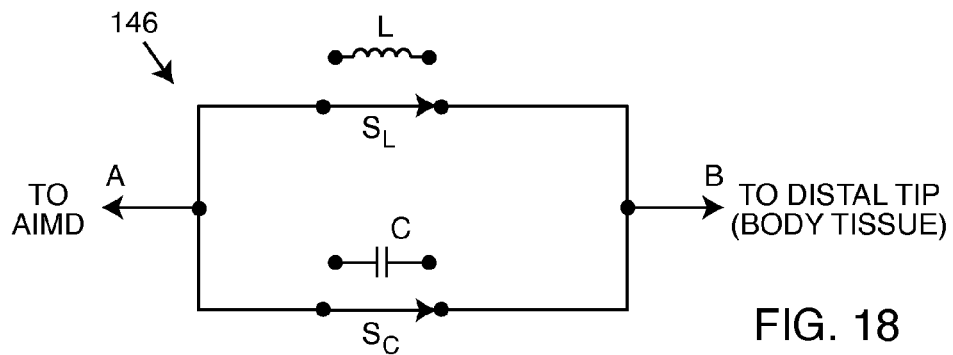
FIG. 18 is a schematic representation of the novel band stop tank filter of the present invention, using switches to illustrate its function at various frequencies.

FIG. 18 is a representation of the novel band stop tank filter 146 using switches that open and close at various frequencies to illustrate its function. Inductor L has been replaced with a switch $S_L$. When the impedance of the inductor is quite low, the switch $S_L$ will be closed. When the impedance or inductive reactance of the inductor is high, the switch $S_L$ will be shown open. There is a corresponding analogy for the capacitor element C. When the capacitive reactance looks like a very low impedance, the capacitor switch $S_C$ will be shown closed. When the capacitive reactance is shown as a very high impedance, the switch $S_C$ will be shown open. This analogy is best understood by referring to FIGS. 19, 20 and 21.

Figure 19:
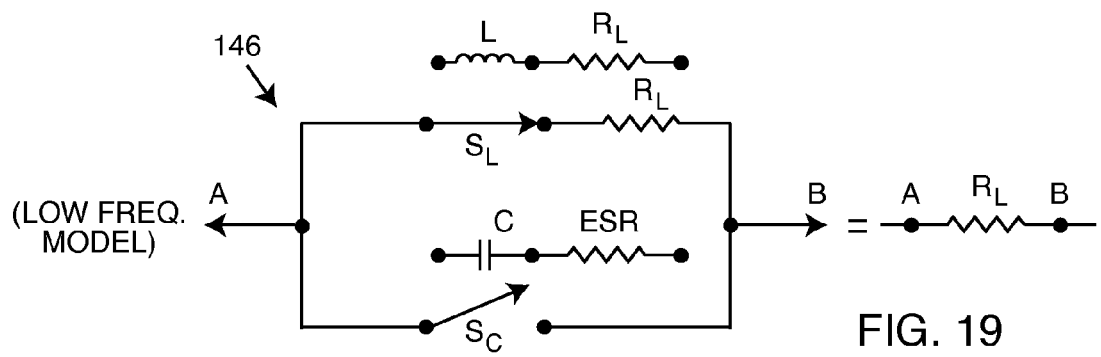
FIG. 19 is a schematic diagram similar to FIG. 18, illustrating the low frequency model of the band stop filter.

FIG. 19 is the low frequency model of the band stop filter 146. At low frequencies, capacitors tend to look like open circuits and inductors tend to look like short circuits. Accordingly, switch $S_L$ is closed and switch $S_C$ is open. This is an indication that at frequencies below the resonant frequency of the band stop filter 146 that currents will flow only through the inductor element and its corresponding resistance $R_L$. This is an important consideration for the present invention that low frequency biological signals not be attenuated. For example, in a cardiac pacemaker, frequencies of interest generally fall between 10 Hz and 1000 Hz. Pacemaker pacing pulses fall within this general frequency range. In addition, the implantable medical device is also sensing biological frequencies in the same frequency range. Accordingly, such signals must be able to flow readily through the band stop filter's inductor element. A great deal of attention should be paid to the inductor design so that it has a very high quality factor (Q) and a very low value of parasitic series resistance $R_L$.

Figure 20:
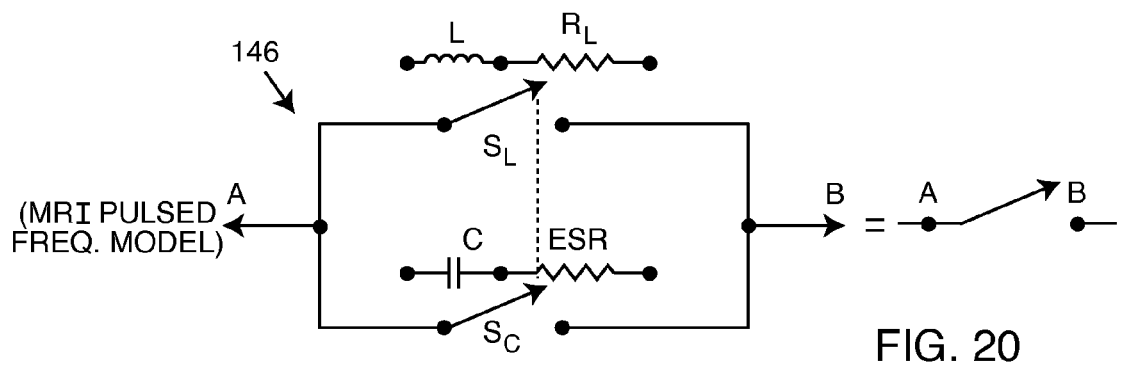
FIG. 20 is a schematic diagram similar to FIGS. 18 and 19, illustrating the model of the band stop filter of the present invention at its resonant frequency.

FIG. 20 is a model of the novel band stop filter 146 at its resonant frequency. By definition, when a parallel tank circuit is at resonance, it presents a very high impedance to the overall circuit. Accordingly, both switches $S_L$ and $S_C$ are shown open. For example, this is how the band stop filter 146 prevents the flow of MRI currents through pacemaker lead wires and/or into body tissue at a selected MRI RF pulsed frequency.

Figure 21:
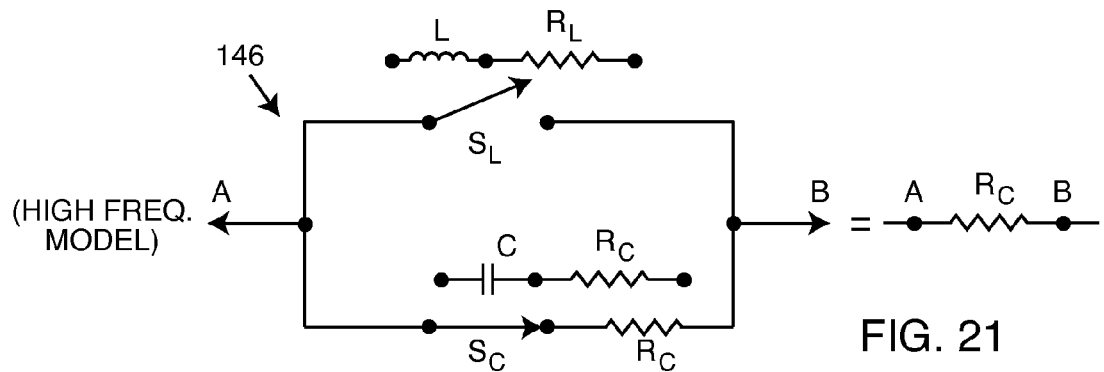
FIG. 21 is a schematic diagram similar to FIGS. 18-20, illustrating a model of the band stop filter at high frequencies well above the resonant frequency.

FIG. 21 is a model of the band stop filter 146 at high frequency. At high frequencies, inductors tend to look like open circuits. Accordingly, switch $S_L$ is shown open. At high frequencies, ideal capacitors tend to look like short circuits, hence switch $S_C$ is closed. It should be noted that real capacitors are not ideal and tend to degrade in performance at high frequency. This is due to the capacitor's equivalent series inductance and equivalent series resistance. Fortunately, for the present invention, it is not important how lossy (resistive) the capacitor element C gets at high frequency. This will only serve to attenuate unwanted electromagnetic interference from flowing in the lead wire system. Accordingly, in terms of biological signals, the equivalent series resistance $R_C$ and resulting quality factor of the capacitor element C is not nearly as important as the quality factor of the inductor element L. The equation for inductive reactance ($X_L$) is given in FIG. 15. The capacitor reactance equation ($X_C$) is also given in FIG. 15. As one can see, when one inserts zero or infinity for the frequency, one derives the fact that at very low frequencies inductors tend to look like short circuits and capacitors tend to look like open circuits. By inserting a very high frequency into the same equations, one can see that at very high frequency ideal inductors look like an infinite or open impedance and ideal capacitors look like a very low or short circuit impedance.

Figure 22:
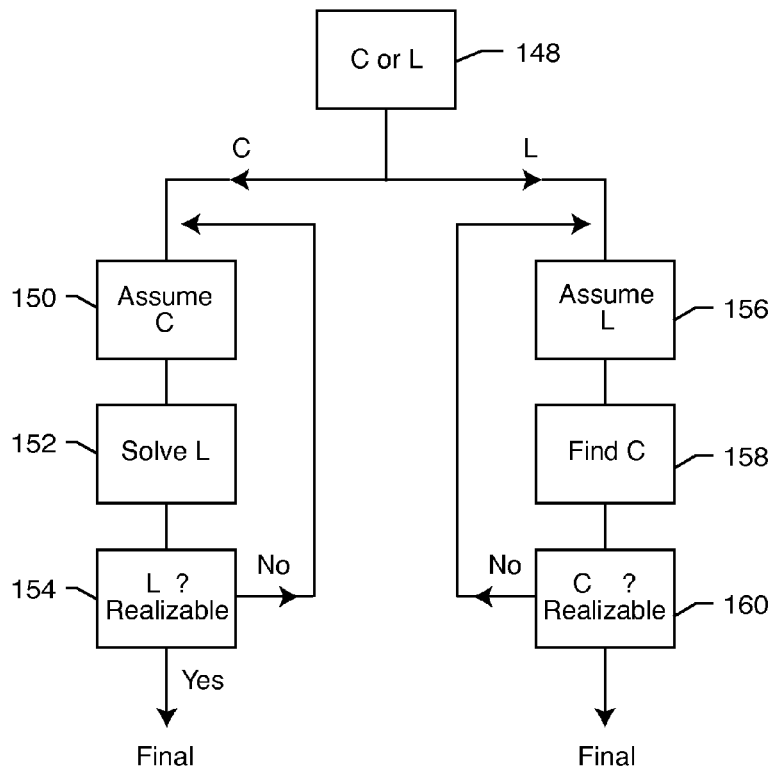
FIG. 22 is a decision tree block diagram illustrating a process for designing the band stop filters of the present invention.

FIG. 22 is a decision tree block diagram that better illustrates the design process herein. Block 148 is an initial decision step the designer must make. For illustrative purposes, we will start with a value of capacitance that is convenient. This value of capacitance is generally going to relate to the amount of space available in the AIMD lead wire system and other factors. These values for practical purposes generally range in capacitance value from a few tens of picofarads up to about 10,000 picofarads. This puts practical boundaries on the amount of capacitance that can be effectively packaged within the scope of the present invention. However, that is not intended to limit the general principles of the present invention, but just describe a preferred embodiment. Accordingly, in the preferred embodiment, one will select capacitance values generally ranging from 100 picofarads up to about 4000 picofarads and then solve for a corresponding inductance value required to be self-resonant at the selected telemetry frequency. Referring back to FIG. 22, one makes the decision whether the design was C first or L first. If one makes a decision to assume a capacitance value C first then one is directed to the left to block 150. In block 150, one does an assessment of the overall packaging requirements of a distal TIP 142 band stop filter 146 and then assumes a realizable capacitance value. So, in decision block 150, we assume a capacitor value. We then solve the resonant tank equation $f_r$ from FIG. 12 at block 152 for the required value of inductance (L). We then look at a number of inductor designs to see if the inductance value is realizable within the space, parasitic resistance $R_C$, and other constraints of the design. If the inductance value is realizable, then we go on to block 154 and finalize the design. If the inductance value is not realizable within the physical and practical constraints, then we need to go back to block 150 and assume a new value of capacitance. One may go around this loop a number of times until one finally comes up with a compatible capacitor and an inductor design. In some cases, one will not be able to achieve a final design using this alone. In other words, one may have to use a custom capacitor value or design in order to achieve a result that meets all of the design criteria. That is, a capacitor design with high enough internal losses $R_C$ and an inductor design with low internal loss $R_L$ such that the band stop filter 146 has the required quality factor (Q), that it be small enough in size, that it have sufficient current and high voltage handling capabilities and the like. In other words, one has to consider all of the design criteria in going through this decision tree.

In the case where one has gone through the left hand decision tree consisting of blocks 150, 152 and 154 a number of times and keeps coming up with a "no," then one has to assume a realizable value of inductance and go to the right hand decision tree starting at block 156. One then assumes a realizable value of inductance (L) with a low enough series resistance for the inductor $R_L$ such that it will work and fit into the design space and guidelines. After one assumes that value of inductance, one then goes to decision block 158 and solves the equation C in FIG. 12 for the required amount of capacitance. After one finds the desired amount of capacitance C, one then determines whether that custom value of capacitance will fit into the design parameters. If the capacitance value that is determined in step 160 is realizable, then one goes on and finalizes the design. However, if it is not realizable, then one can go back up to step 156, assume a different value of L and go through the decision tree again. This is done over and over until one finds combinations of L and C that are practical for the overall design.

For purposes of the present invention, it is possible to use series discrete inductors or parallel discrete capacitors to achieve the same overall result. For example, in the case of the inductor element L, it would be possible to use two, three or even more (n) individual inductor elements in series. The same is true for the capacitor element that appears in the parallel tank filter 146. By adding or subtracting capacitors in parallel, we are also able to adjust the total capacitance that ends up resonating in parallel with the inductance.

It is also possible to use a single inductive component that has significant parasitic capacitance between its adjacent turns. A careful designer using multiple turns could create enough parasitic capacitance such that the coil becomes self-resonant at a predetermined frequency. In this case, the predetermined frequency would be the MRI pulsed frequency.

Figure 23:
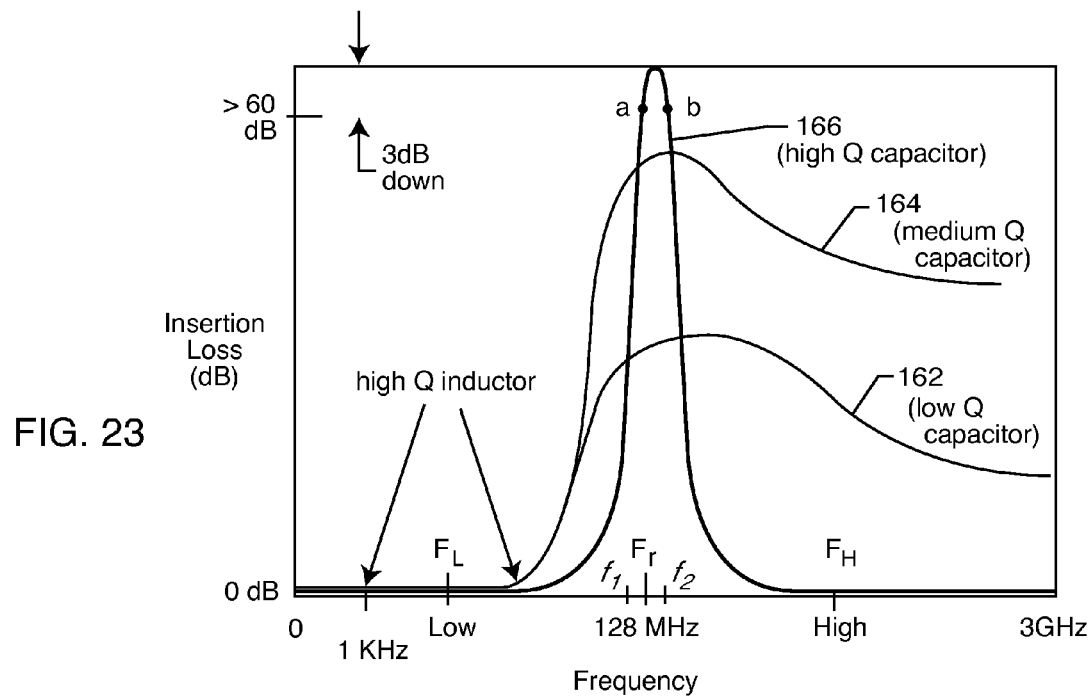
FIG. 23 is graph of insertion loss versus frequency for band stop filters having high Q inductors and differing quality "Q" factors.

Efficiency of the overall tank circuit 146 is also measured in terms of a quality factor, Q, although this factor is defined differently than the one previously mentioned for discrete capacitors and inductors. The circuit Q is typically expressed using the following equation:

$$Q = \frac{f_r}{\Delta f_{3\,dB}}$$

Where $f_r$ is the resonance frequency, and $\Delta f_{3dB}$ shown as points a and b in FIG. 23, is the bandwidth of the band stop filter 146. Bandwidth is typically taken as the difference between the two measured frequencies, $f_1$ and $f_2$, at the 3 dB loss points as measured on an insertion loss chart, and the resonance frequency is the average between $f_1$ and $f_2$. As can be seen in this relationship, higher Q values result in a narrower 3 dB bandwidth.

Material and application parameters must be taken into consideration when designing tank filters. Most capacitor dielectric materials age 1%-5% in capacitance values per decade of time elapsed, which can result in a shift of the resonance frequency of upwards of 2.5%. In a high-Q filter, this could result in a significant and detrimental drop in the band stop filter performance. A lower-Q filter would minimize the effects of resonance shift and would allow a wider frequency band through the filter. However, very low Q filters display lower than desirable attenuation behavior at the desired band stop frequency (see FIG. 23, curve 162). For this reason, the optimum Q for the band stop filter of the present invention will embody a high Q inductor L and a relatively low Q capacitor C which will result in a medium Q tank filter as shown in curve 164 of FIG. 23.

Accordingly, the "Q" or quality factor of the tank circuit is very important. As mentioned, it is desirable to have a very low loss circuit at low frequencies such that the biological signals not be undesirably attenuated. The quality factor not only determines the loss of the filter, but also affects its 3 dB bandwidth. If one does a plot of the filter response curve (Bode plot), the 3 dB bandwidth determines how sharply the filter will rise and fall. With reference to curve 166 of FIG. 23, for a tank that is resonant at 128 MHz, an ideal response would be one that had infinite attenuation at 128 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either. Capacitors have internal resistance known as equivalent series resistance and also have small amounts of inductance. Accordingly, the practical realization of a circuit, to accomplish the purposes of the present invention, is a challenging one.

The performance of the circuit is directly related to the efficiency of both the inductor and the capacitor; the less efficient each component is, the more heat loss that results, and this can be expressed by the addition of resistor elements to the ideal circuit diagram. The effect of lower Q in the tank circuit is to broaden the resonance peak about the resonance frequency. By deliberately using a low Q capacitor, one can broaden the resonance such that a high impedance (high attenuation) is presented at multiple MRI RF frequencies, for example 64 MHz and 128 MHz.

Referring again to FIG. 23, one can see curve 164 wherein a low resistive loss high Q inductor has been used in combination with a relatively high ESR low Q capacitor. This has a very desirable effect in that at very low frequencies, the impedance of the tank circuit 146 is essentially zero ohms (or zero dB loss). This means that biologic frequencies are not undesirably attenuated. However, one can see that the 3 db bandwidth is much larger. This is desirable as it will block multiple RF frequencies. As one goes even higher in frequency, curve 164 will desirably attenuate other high frequency EMI signals, such as those from cellular telephones, microwave ovens and the like. Accordingly, it is often desirable that very low loss inductors be used in combination with relatively high loss (and/or high inductance) capacitors to achieve a medium or lower Q band stop filter. Again referring to FIG. 23, one can see that if the Q of the overall circuit or of the individual components becomes too low, then we have a serious degradation in the overall attenuation of the band stop filter at the MRI pulse frequencies. Accordingly, a careful balance between component design and tank circuit Q must be achieved.

Referring once again to FIG. 17, one can also increase the value of $R_C$ by adding a separate discrete component in series with the capacitor element. For example, one could install a small capacitor chip that had a very low equivalent series resistance and place it in series with a resistor chip. This would be done to deliberately raise the value of $R_C$ in the circuit as shown in FIG. 17. By carefully adjusting this value of $R_C$, one could then achieve the ideal curve 164 as shown in FIG. 23.

Figure 24:
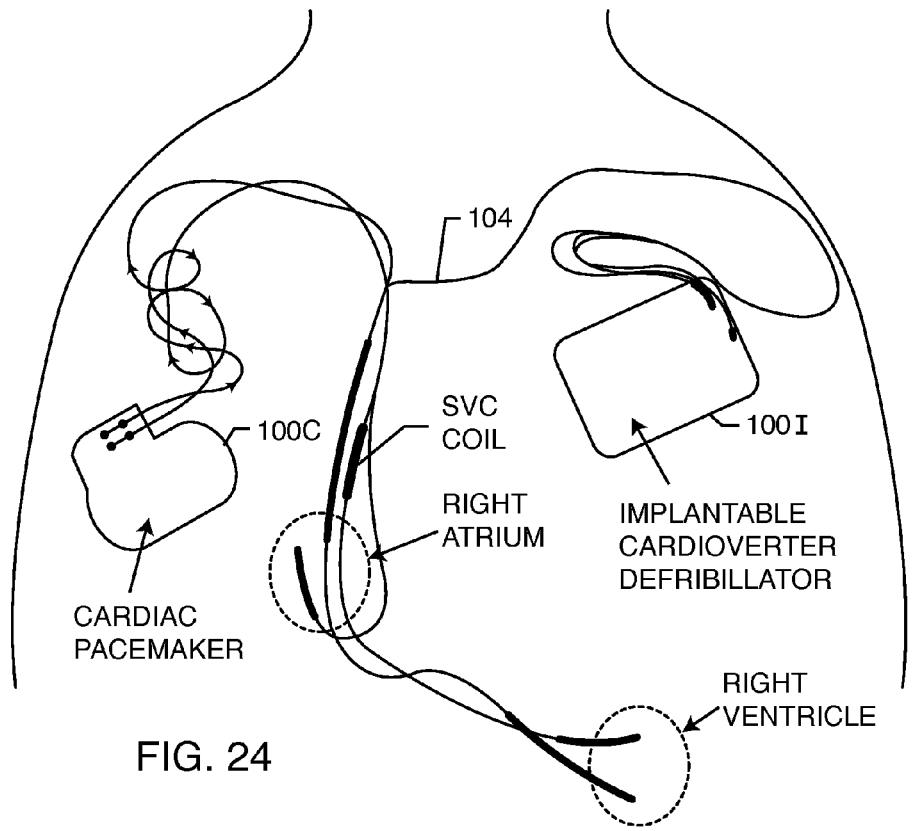
FIG. 24 is a tracing of an exemplary patient x-ray showing an implanted pacemaker and cardioverter defibrillator and corresponding lead wire system.

FIG. 24 is a tracing of an actual patient X-ray. This particular patient required both a cardiac pacemaker 100C and an implantable cardioverter defibrillator 100I. The corresponding lead wire system 104, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

Referring again to FIG. 24, one can see that from the pacemaker 100C, there is an electrode in both the right atrium and in the right ventricle. Both these involve a TIP and RING electrode. In the industry, this is known as a dual chamber bipolar lead wire system. Accordingly, the band stop filters 146 of the present invention would need to be placed at least in the distal TIP in the right atrium and the distal TIP in the right ventricle from the cardiac pacemaker. One can also see that the implantable cardioverter defibrillator (ICD) 100I is implanted directly into the right ventricle. Its shocking TIP and perhaps its super vena cava (SVC) shock coil would also require a band stop filters of the present invention so that MRI exposure cannot induce excessive currents into the associated lead wire system (S). Modern implantable cardioverter defibrillators (ICDs) incorporate both pacing and cardioverting (shock) features. Accordingly, it is becoming quite rare for a patient to have a lead wire layout as shown in the X-ray of FIG. 24. However, the number of electrodes remains the same. There are also newer combined pacemaker/ICD systems which include biventricular pacemaking (pacing of the left ventricle). These systems can have as many as 9 to even 12 lead wires.

Figure 25:
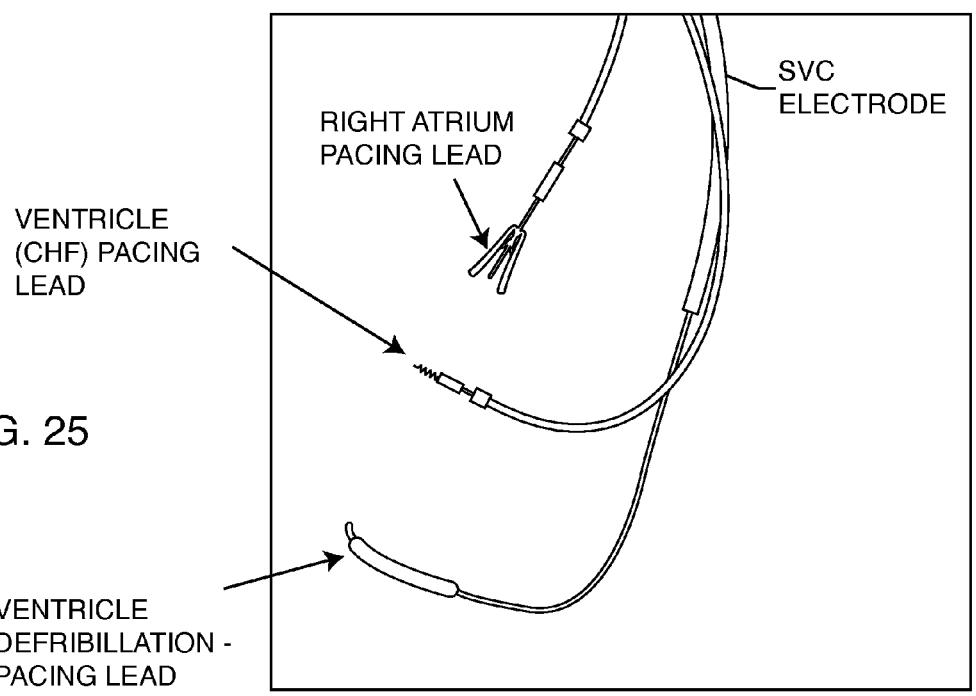
FIG. 25 is a line drawings of an exemplary patent cardiac x-ray of a bi-ventricular lead wire system.

FIG. 25 is a line drawing of an actual patient cardiac X-ray of one of the newer bi-ventricular lead wire systems with various types of electrode TIPS shown. The new bi-ventricular systems are being used to treat congestive heart failure, and make it possible to implant leads outside of the left ventricle. This makes for a very efficient pacing system; however, the lead wire system 104 is quite complex. When a lead wire system 104, such as those described in FIGS. 8, 9, 10 and 11, are exposed to a time varying electromagnetic field, electric currents can be induced into such lead wire systems. For the bi-ventricular system, band stop filters 146 would be required at each of the three distal TIPs and optionally at RING and SVC locations.

Figure 26:
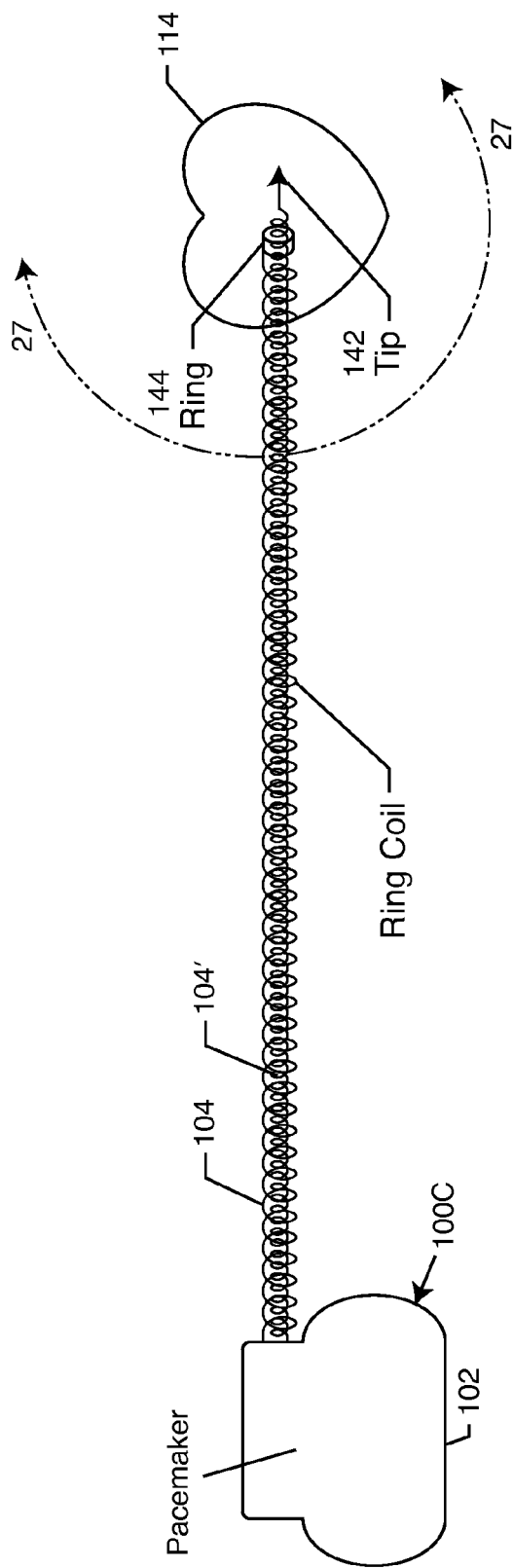
FIG. 26 illustrates a bipolar cardiac pacemaker lead wire showing the distal TIP and the distal RING electrodes.

FIG. 26 illustrates a single chamber bipolar cardiac pacemaker lead wire showing the distal TIP 142 and the distal RING 144 electrodes. This is a spiral wound system where the RING coil 104 is wrapped around the TIP coil 104'. There are other types of pacemaker lead wire systems in which these two leads lay parallel to one another (known as a bifilar lead system).

Figure 27:
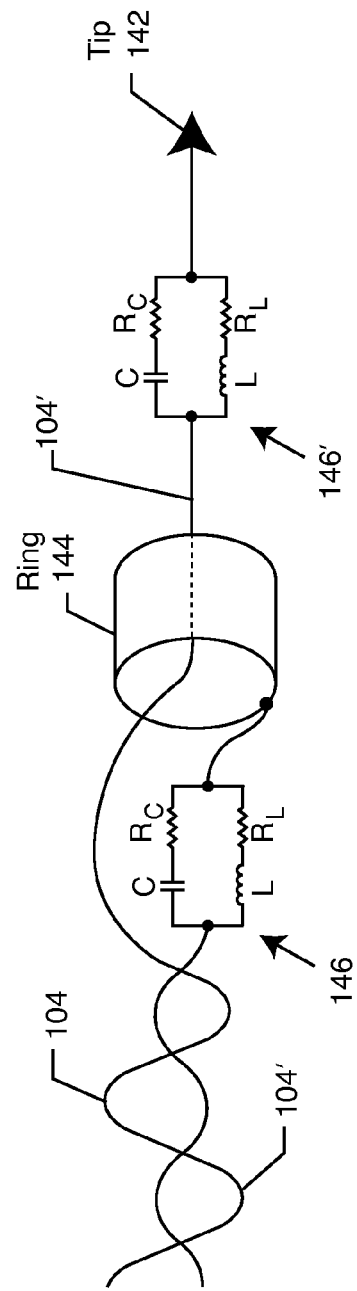
FIG. 27 is an enlarged, fragmented schematic illustration of the area illustrated by the line 27-27 in FIG. 26.

FIG. 27 is a schematic illustration of the area 27-27 in FIG. 26. In the area of the distal TIP 142 and RING 144 electrodes, band stop filters 146 and 146' have been placed in series with each of the respective TIP and RING circuits. Accordingly, at MRI pulsed frequencies, an open circuit will be presented thereby stopping the flow of undesirable RF current.

Figure 28:
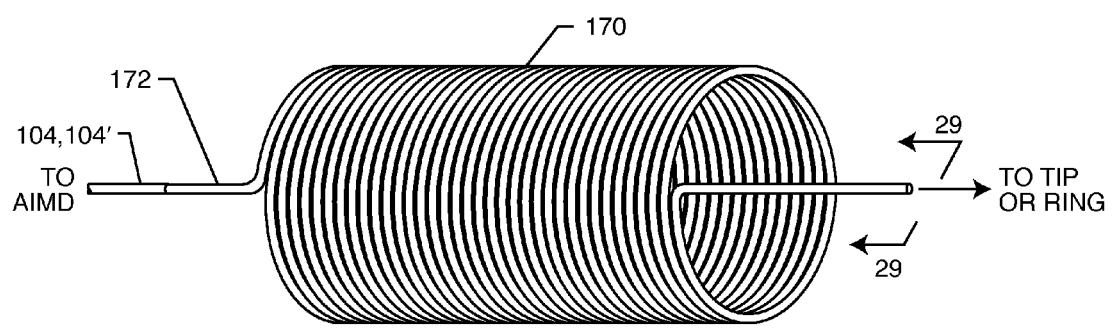
FIG. 28 is a perspective view of a single-layer inductive coil.

FIG. 28 illustrates an alternate form of a bandstop filter previously illustrated in FIG. 27 as elements 146 and 146'. It was earlier stated that, "It is also possible to use a single inductive component that has significant parasitic capacitance between its adjacent turns. A careful designer, using multiple turns, could create enough parasitic capacitance such that the coil becomes self-resonant at a predetermined frequency. In this case, the predetermined frequency would be the MRI RF-pulsed frequency." Referring once again to FIG. 28, lead conductor 104, 104' is connected to a single layer resonant coil structure 170. It is well known to those skilled in the art that coiling of a conductor, as shown in FIG. 28, creates a single layer solenoid inductor. In order to form an inductor, it is also well known in the art that the conductor material be insulated. For example, various types of insulative wire are available in the industry for manufacturing inductor coils.

Figure 29:
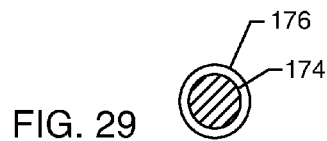
FIG. 29 is a sectional view taken along line 29-29 of FIG. 28 illustrating a conductive core with a dielectric coating.

FIG. 29 is a sectional view taken from section 29-29 from FIG. 28 illustrating that the inductor coil conductor 172 consists of a solid metallic center 174 which is surrounded by an insulative material 176. In the present invention, the insulation material 176 is very important. This is because parasitic capacitance is formed between adjacent turns of coil 170 causing it to become self-resonant at an MRI RF-pulsed frequency. Both the dielectric constant of the insulation and the thickness of the insulation are very important. In general, capacitance is equal to the dielectric constant times the area times the number of turns divided by the dielectric thickness. For example, if one makes the dielectric thickness 176 very thin and winds the coil turns very tightly together, the parasitic capacitance will increase. The equation for resonant frequency is previously described in FIGS. 12 and 13. The self-resonant inductor structure 170 has been designed, for example, to replace tank filters 146 and/or 146' as previously illustrated in FIG. 27. In other words, for a typical bipolar pacemaker application, it would be desirable to have a self-resonant inductor 170 near or adjacent both the tip electrode and the ring electrode as previously illustrated in FIG. 27. It will be obvious to those skilled in the art that the self-resonant coil or tank filter of FIG. 28 could be put in series with any implantable lead conductor, such as those used in neuro-stimulator applications and the like. A more complete example of these types of AIMDs is previously described in FIG. 1. In addition, the self-resonant inductor structure 170 would also be very useful for a probe or catheter 100K, as shown in FIG. 1, during MRI-guided intervention procedures, such as RF ablation.

Figure 30:
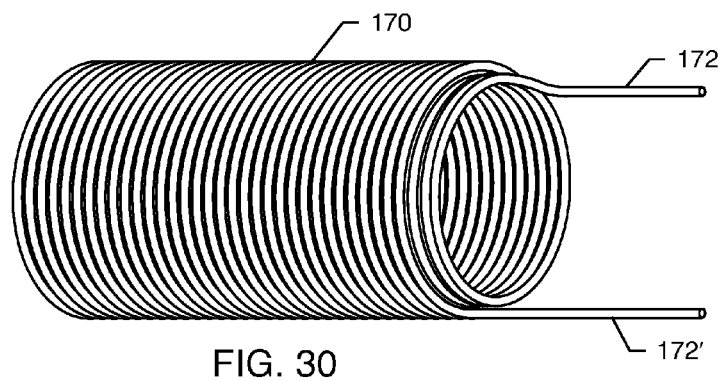
FIG. 30 is a perspective view of a two-layer inductive coil.

In designing a tank filter (otherwise known as a bandstop filter) for medical implant applications, it is important to have a very high impedance or insertion loss both at resonance and also across the 3-dB bandwidth. In this regard, the L/C ratio is very important. The higher the inductance to capacitance ratio, the higher the impedance will generally be at resonance. Accordingly, a large amount of inductance is preferable with a relatively small amount of capacitance. Therefore, the single layer coil, as illustrated in FIG. 28 is not a particularly preferred embodiment. A better approach would be to use a two layer coil, as illustrated in FIG. 30. In this case, a single length of wire 172 has been wounded in one direction and then wound back, forming a two-layer self-resonant inductor. Parasitic capacitance is still formed between the adjacent turns and also between the coils of the inner layer and the outer layer. However, the structure shown in FIG. 30 is not a preferred embodiment for human implant. The reason for this is the insulative conductor 172 and 172' that forms the coil inductor both emerge from one end. In this case, both are shown emerging from the right side. This makes this type of structure particularly inconvenient for placement in series in an implantable lead conductor. Implantable lead conductors must be very small in diameter for transvenous insertion or for tunneling through human tissues.

Figure 31:
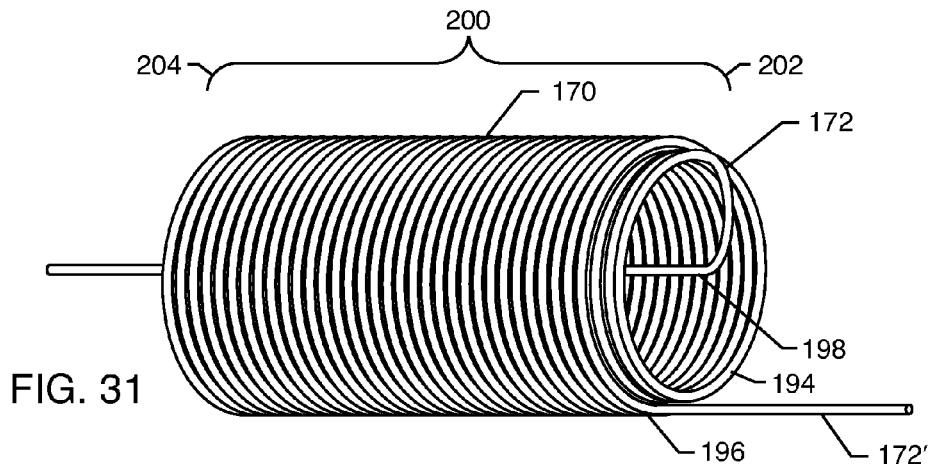
FIG. 31 is a perspective view of another embodiment of a two-layer inductive coil.

FIG. 31 illustrates that wire 172 can be returned back through the center of the coil structure thereby actually placing conductors 172 and 172' actually inline. This makes this type of structure ideal to place the self-resonant coil (tank filter) in series with an implantable lead conductor. It will also be obvious that the return wire could be placed on the outside of the coil. However, this is also not preferred because it would increase the diameter of the coil. In greater detail, the self-resonant inductor 170 is connected in series along a portion of the length of the lead conductor 104. The self-resonant inductor 170 includes a single length of conductive material including a dielectric coating 176 substantially surrounding the single length of conductive material. The self-resonant inductor 170 includes a first coiled or spiral conductor 194 disposed along an inductor section 200 spanning in a first direction from a first location 202 to a second location 204. A second coiled or spiral conductor 196 is disposed along the inductor section 200 spanning in a second direction from the second location 204 to the first location 202. Note that the second direction is opposite the first direction. A third (straight or non-coiled) conductor 198 is disposed along the inductor section 200 spanning in the first direction from the first location 202 to the second location 204. Note that the inductor 170 can be flipped to be connected in series along the lead 104 in either direction. Also note that the straight return conductor 198 may be configured to attach or start from the inside coil 194 (as shown) or alternatively attach or start from the outside coil 196 (not shown).

Figure 32:
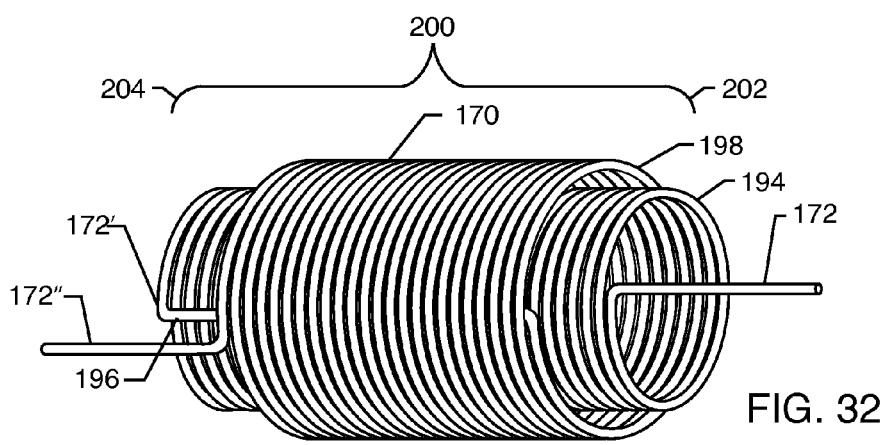
FIG. 32 is a perspective view of another embodiment of a two-layer inductive coil with a straight return wire between an inner and outer coil.

FIG. 32 is very similar to FIG. 30, except that the return wire 172' is disposed between the inner coiled conductor 172 and the outer coiled conductor 172". The return wire 172' may be coiled as well, or as shown here, a straight wire conductor 172' connecting the inner coiled conductor 172 and the outer coiled conductor 172". In greater detail, the self-resonant inductor 170 is connected in series along a portion of the length of the lead conductor 104. The self-resonant inductor 170 includes a single length of conductive material including a dielectric coating 176 substantially surrounding the single length of conductive material. The self-resonant inductor 170 includes a first coiled or spiral conductor 194 disposed along an inductor section 200 spanning in a first direction from a first location 202 to a second location 204. A second (straight or non-coiled) conductor 196 is disposed along the inductor section 200 in a second direction opposite the first direction spanning from the second location 204 to the first location 202. A third coiled or spiral conductor 198 is disposed along the inductor section 200 spanning in the first direction from the first location 202 to the second location 204.

Figure 33:
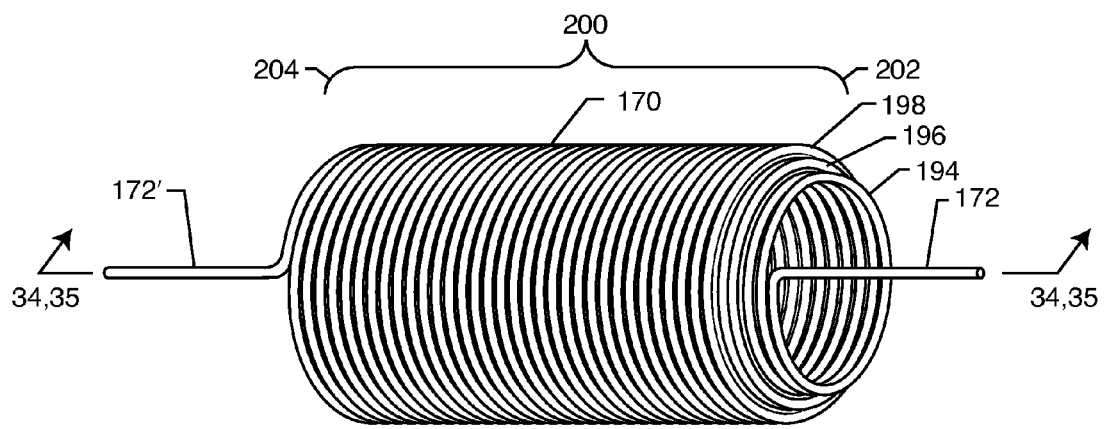
FIG. 33 is a perspective view of a three-layer inductive coil.

FIG. 33 is very similar to FIG. 30 except this is a three-layer self-resonant coil construction. In a preferred embodiment, the self-resonant coil of FIG. 33 is wound from one continuous conductor starting from the right where the turns are wrapped around a mandrel (not shown) all the way to the left and then wrapped back over itself to the right and then wrapped back over itself tightly to the left at point 172'. In greater detail, the self-resonant inductor 170 is connected in series along a portion of the length of the lead conductor 104. The self-resonant inductor 170 may be made from a single length of conductive material comprising a dielectric coating 176 substantially surrounding the single length of conductive material. The self-resonant inductor 170 includes a first insulated coiled or spiral conductor 194 disposed along an inductor section 200 spanning in a first direction from a first location 202 to a second location 204. A second insulated coiled or spiral conductor 196 is disposed along the inductor section 200 spanning in a second direction from the second location 204 to the first location 202. Note that the second direction is opposite the first direction. A third insulated coiled or spiral conductor 198 is disposed along the inductor section 200 spanning in the first direction from the first location 202 to the second location 204.

Figure 34:
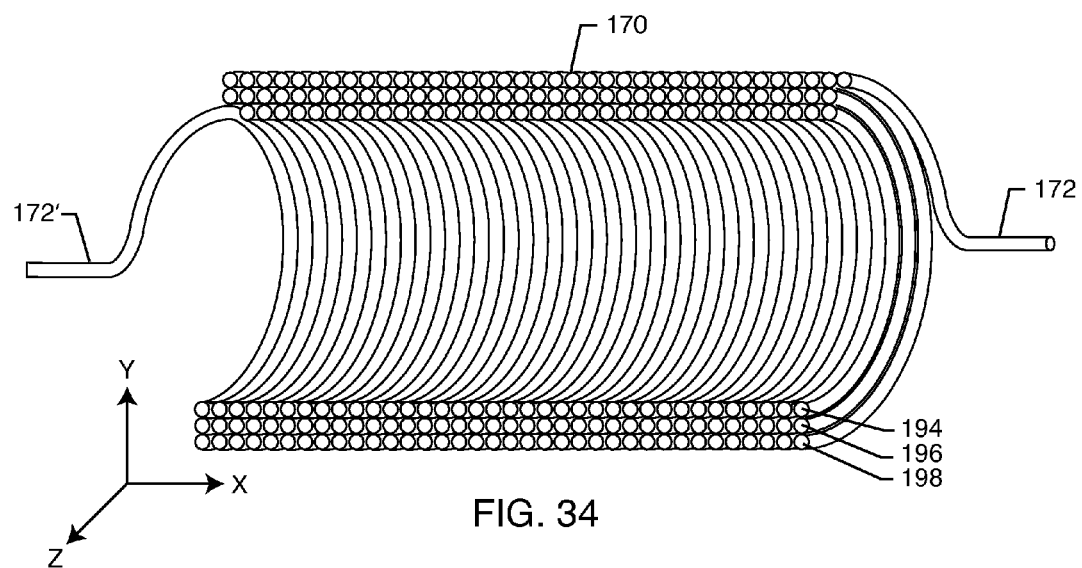
FIG. 34 is a sectional perspective view taken along line 34-34 of FIG. 33.

FIG. 34 is a cross-sectional view taken from section 34-34 from FIG. 33. In a preferred embodiment, the three layers are tightly packed in both the x and y direction as shown. For simplicity, in drawings 28 and 30 through 36, the wire insulation is not shown, but it will be well understood that it is always present as illustrated in FIG. 29. FIG. 34 is a particularly sufficient structure, in that, it provides a very high amount of inductance due to the overlapping solenoid turns while at the same time providing sufficient parasitic capacitance so that it can be made to be self-resonant at an MRI RF-pulsed frequency.

Referring back to FIG. 29, the diameter of the center core and the resistivity of the center core 174 are also very important as resistance of the inductor depends on cross sectional area and resistivity of the conductor wire. The resistance of the conductor is very important in determining the Q and the resulting 3-dB bandwidth of the completed tank filter. One is referred to FIG. 16 to element $R_L$ to see where this resistance appears in the circuit. In general, if one uses relatively high resistivity and very small diameter wire, the resistance will go up and the Q of the inductor will go down. This results in an increased 3-dB bandwidth as previously described in FIG. 23. When the resistance of the inductor is particularly high, one would have a resulting low Q curve, previously illustrated as curve 162 in FIG. 23. On the other hand, if one were to use relatively large diameter wire with very low resistivity, then a high Q tank filter would result, which would be a resonant curve more like curve 166 in FIG. 23. In general, the designer balances the number of turns, the wire size, the wire conductivity, the insulation dielectric properties and the insulation thickness all to produce a self-resonant coil, which will have at least 15-dB of attenuation across its 3-dB resonant frequency range and will also present no more than 3-dB of attenuation from zero (0) to one (1) kHz, which is the biologic frequency range. All of this is previously illustrated in FIG. 23.

Figure 35:
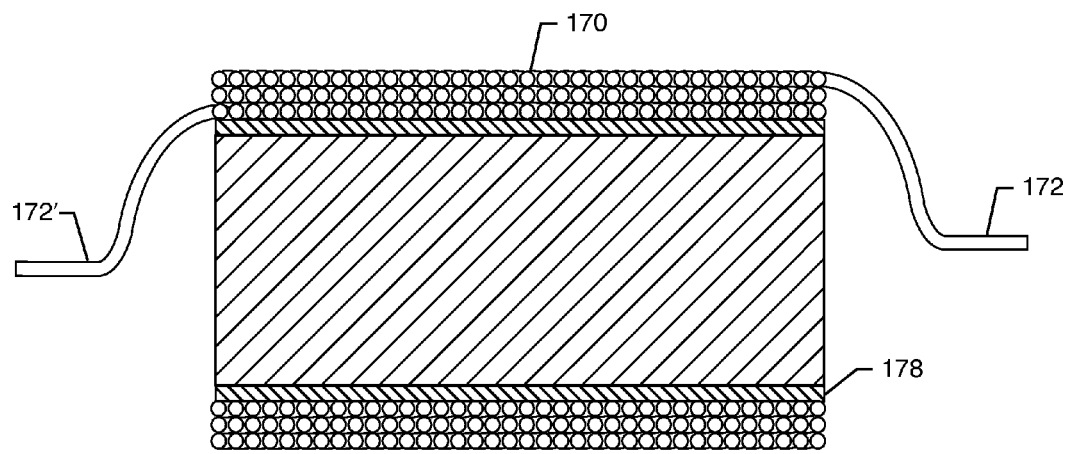
FIG. 35 is a sectional side view taken along line 35-35 of FIG. 33.

As mentioned previously, the coil structures of FIGS. 28 through 34 are wound on a mandrel (not shown) and then the mandrel was removed. In a preferred embodiment, the wires being wound would have insulation material that is thermoplastic. By raising the temperature of the wound structure, either segmentally or in its entirety, and either during the layered winding process or upon completion of the desired number of layers, the adjacent coils are then bonded to each other so that the coil becomes free standing. Alternatively, one could use the mandrel 178, as illustrated in FIG. 35 and leave it in place to provide structural rigidity. The coil turns could be overlaid with some sort of a thermoplastic insulative material to hold them all tightly packed in place. One could also put a heat shrink tubing the like to hold it mechanically together as well. Referring once again to FIG. 35, the mandrel 178 could be hollow or it could be solid all the way through the center. In the case of an active fixation tip electrode, a preferred embodiment would be a solid core in order to transmit maximum torque during physician implantation of the active fixation or screw tip.

Figure 36:
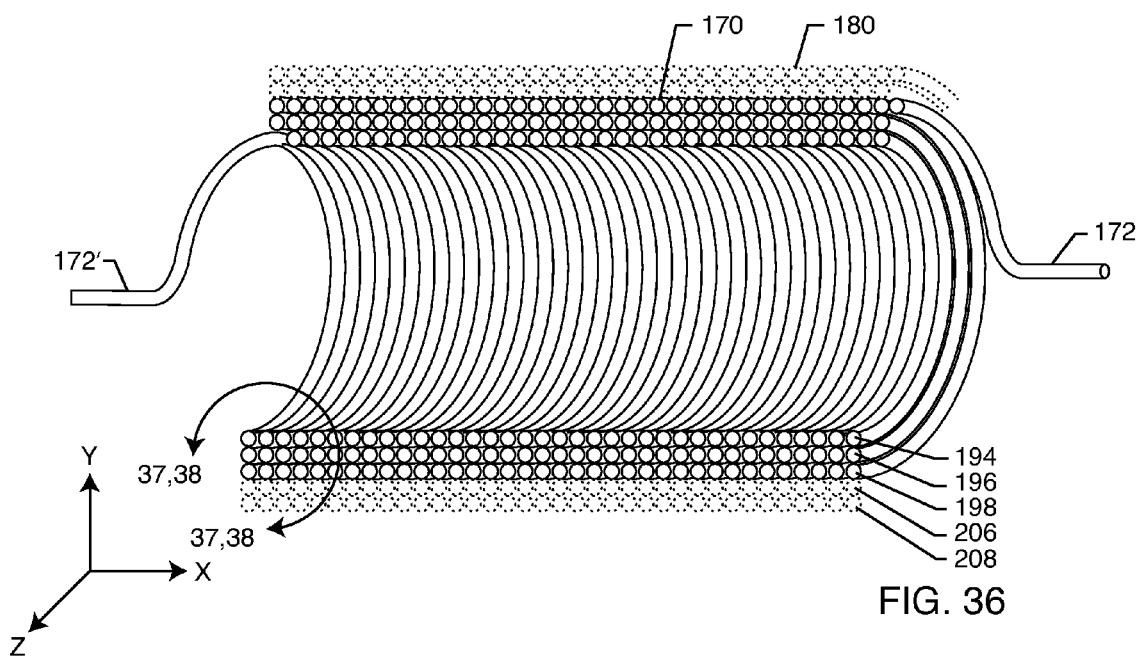
FIG. 36 is a sectional side view similar to FIG. 34 now showing a plurality of additional coil layers.

FIG. 36 is very similar to FIG. 34, which was a 3-layer inductor with coil layers 194, 196 and 198. The purpose of FIG. 36 is to illustrate that any number of coil layers "n" can be added to the inductors previously described in FIGS. 28 through 35. Specifically, referring to FIG. 35, a 3-layer coil is depicted. In forming a 3-layer coil, a continuous wire is wound from left to right and then from right to left and once again from left to right. As a result, a continuous conductor that terminates at opposite axial ends of the multilayer self-resonant inductor, shown as 172 and 172', is produced. It will be obvious to one skilled in the art that it will be very easy to install this structure in series anywhere along the length of an implantable lead conductor. Referring once again to FIG. 36, any number of additional layers 206, 208 or even "n" layers, meaning any number of layers, can be added to this wound structure. When the number of layers added is an even number, such as having only layers 194, 196, 198 and 206, then the inductor as shown in FIG. 36 would require a return wire as previously illustrated in FIG. 31 or 32. The reason for this is that it is important that the self-resonant inductor end connections 172 and 172' be at opposite ends of the structure and be aligned axially for simple insertion into an implantable lead conductor. Implantable leads are inserted transvenously, epicardially or by tunneling through patient tissue. Accordingly, they must be very small in diameter. The optimal place for the return wire (when "n" is an even number) is back through the center of the coil structure, as shown in FIG. 31. Of course, it will be obvious to those skilled in the art that a return wire could be on the outside (not optimal) of the coil layers, or it could even be interleaved between adjacent coil layers (also not optimal). Interleaving between coil layers was previously illustrated in FIG. 32.

Referring once again to FIG. 36, an odd number of layers illustrated as comprising wire 194, 196, 198, 206 and 208, would produce a 5-layer self-resonant solenoid/inductor. In this case, when initiating the winding at 172' and then winding from left to right, the first layer 194 is formed. Then, layer 196 is formed by winding back in the opposite direction until the location in the general area of 172' is reached. This forms the second layer of the inductor. The third layer 198 is then formed by winding once again from left to right stopping the winding in close proximity to the end of the inductor 172. With the same continuous piece of wire, the fourth layer 206 is then formed by winding from the right back to the left. The fifth layer 208 (which in this example is the last or outer layer) is formed by winding, once again, from the left, in the general area of 172' back to the right and would terminate at 172 (not shown). This may seem somewhat confusing as location 172 is drawn for a 3-layer inductor, and not an "n"-layer inductor. Nevertheless, it will be obvious to those skilled in the art that the outermost winding in this example produces a 5-layer inductor, whereas the outermost winding as illustrated in FIG. 36 produces a 3-layer inductor. For clarification, each individual layer is wound around the x axis and there are generally any number of coils that are tightly packed adjacent to each other. In general, they are insulated (insulation not shown for simplicity). Each layer is formed by winding the wire back on top of the coils of the previous layer. Each coil layer causes the inductor to get larger in diameter as each additional layer is added.

As defined herein, a coil turn is one complete 360 degree turn of wire around a center axis or mandrel. In general, there can be any number of coil turns along the x axis of the self-resonant solenoid of the present invention. Each coil turn causes the inductor to get longer in length along the x axis. In contrast, a layer is one complete layer of coils that are wound along this x axis thereby forming a complete inductor. This can be a single layer inductor, as previously illustrated in FIG. 28; it could be a 2-layer inductor, as illustrated in FIG. 30; a 3-layer inductor, as illustrated in FIG. 34; or an "n"-layer inductor, as illustrated in FIG. 36. The x, y and z axes are also defined. The x axis is the axis that runs along the central axis of the coil. The diameter of the coil is represented in the y and z axes. The y axis comes straight out of the page at the reader and is perpendicular to the x and z. As used herein, the term "lead" refers to an implantable lead body and its associated insulation and conductors and the like. Also, as used herein, a lead conductor can be one or more wires or other types of conductors that are embedded within the lead. The term "leadwire" generally refers to wires that are inside the AIMD housing and are used for connection between electronic circuits.

Figure 37:
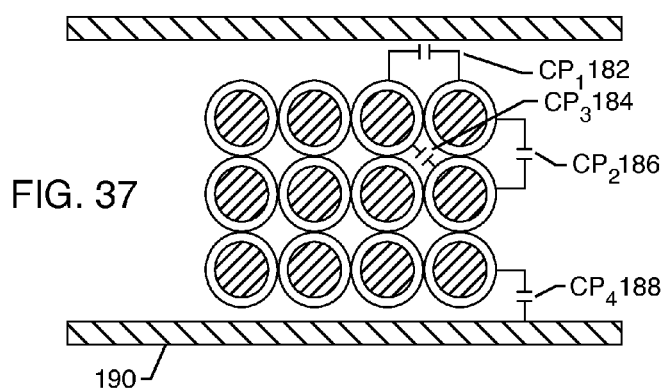
FIG. 37 is an enlarged sectional view taken along line 37-37 of FIG. 36 including a shield.

FIG. 37 is a sectional view taken generally from section 37-37 of FIG. 36. FIG. 37 illustrates a few of the parasitic capacitances just to illustrate the complexity of the structure. A parasitic capacitance 182 is formed between adjacent turns. A parasitic capacitance 186 is also formed between each wire between layers. A parasitic capacitance 184 is also formed along the diagonal between conductors of different layers that are stacked at an angle. If an optional shield 190 is used, an additional parasitic capacitance 188 would also be formed particularly between the outer wires that line the inside of the metal shield 190. Modeling of this parasitic capacitance will be discussed in subsequent drawings.

Figure 38:
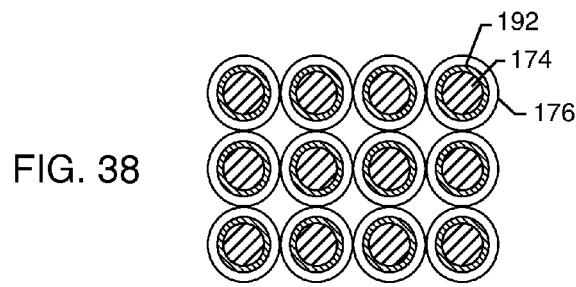
FIG. 38 is an enlarged sectional view taken along line 38-38 of FIG. 36 now showing a conductive inner and outer core.

FIG. 38 is very similar to FIG. 37 and is a cross-sectional view 38-38 taken from FIG. 36. In this case, special cored conductors are used. There is an inner core 174 of a highly conductive material, such as silver and then an outer layer 192, which in general would be of biocompatible material such as MP35N. As previously described in FIG. 29, this would all be overlaid by an insulating material 176.

A wide range of biocompatible materials can be used for both conductor 174 and insulation 176. The conductor wire selection primarily depends on the electromechanical properties of the inductor. Various clad, plated, electroplated, anodized or core combination materials like core wire or filled tubes can be used to optimize the electromechanical properties of the inductor. For the conductive material, a mechanically strong material such as but not limited to MP35N, Nitinol, tungston, tantalum, niobium, Co—Cr—Mo alloys, stainless steel alloys, especially stainless steel alloys with Mo, Ni, Cr combinations, carbon steels, may be used as the outer layer. The core material may be a more highly conductive material but perhaps a less mechanically strong material such as but not limited to silver, platinum and its alloys like platinum-iridium or platinum-tungsten, tantalum, gold, palladium, nitinol, titanium and titanium alloys. It is not necessary that the core material be non-toxic and biocompatible, but it is very important that the outer layer be of non-toxic and biocompatible material. When they are both biocompatible, it will be obvious to those skilled in the art that these materials may be used interchangeably for the inner core or the outer layer depending on the ultimate physical and electrical behavior desired for a particular application. Additionally, the percentage of clad and core material can be adjusted to meet specific electrical and/or mechanical properties for the finished conductor wire.

Insulation material 176 may include a variety of biocompatible materials including various thermoset, thermoplastic or flexible electrically insulative materials. The thermoset family of materials include but is not limited to adhesives, epoxies, elastomers, phenolics, aromatic polyimides, membranes, vulcanized thermosets and fluoropolymers. Also included in this family are filled or reinforced thermoset materials that may include resins or modifiers such as but not limited to pigments, plasticizers or fillers like particulates, short fibers, long fibers, spheres, flakes, nanoparticles, submicron fibers, either isotropically or anistropically dispersed in the thermoset matrix material, or even laminate configurations for same.

The thermoplastic family of materials includes but is not limited to adhesives, elastomers, epoxies and fluoropolymers, some of which are amorphous and some semi-amorphous, some are copolymer blends and some have limited crosslinking which does not compromise the material's flowability at increased temperature. The thermoplastic family of materials may be filled or reinforced with resins or modifiers such as but not limited to pigments, plasticizers or fillers like particulates, short fibers, long fibers, spheres, flakes, nanoparticles, submicron fibers, either isotropically or anistropically dispersed in the thermoplastic matrix material, or even laminate configurations for same. Nonlimiting examples of materials in the thermoplastic family are acrylonitrile butadiene styrene (ABS), acrylics like poly(methyl methacrylate) or PMMA, celluloids, acetates like cellulose acetate or ethylene-vinyl acetate, copolymers like cyclic olefin copolymer, polyethylene, poly(vinyl chloride), polystyrene, acetals, urethanes (for example, carbothane, estane, pellethane, Tecoflex, Tecothane, Texin), nylons (like, Aesno, Besno, Nylon 6, Nylon 6,6, Nylon 12, Pebax, Vestamid), polyether, polyester, polypropylene, polytetrafluoroethylene (PTFE), FEP, PFA, CTFE, ECTFE, PEEK, ETFE, PET, PBT, polyvinylidine fluoride (PVDF), ETTFE, THV, polycarbonate, polyetherimide, polysulfone, parylene, polyethelene, polypropylene, polyether block amids (PEBAX), acid copolymers, and any combination thereof. It is important to note that thermoplastic materials may be selected for applications wherein reliability in performance depends on limited or no deformation of the structure and a solid reinforcement core, such as retaining the wire winding mandrel. In this case, thermal bonding the winding rigidizes the final structure. The degree of rigidity may be selected based on the plasticity or elasticity of the thermoplastic material selected.

Figure 39:
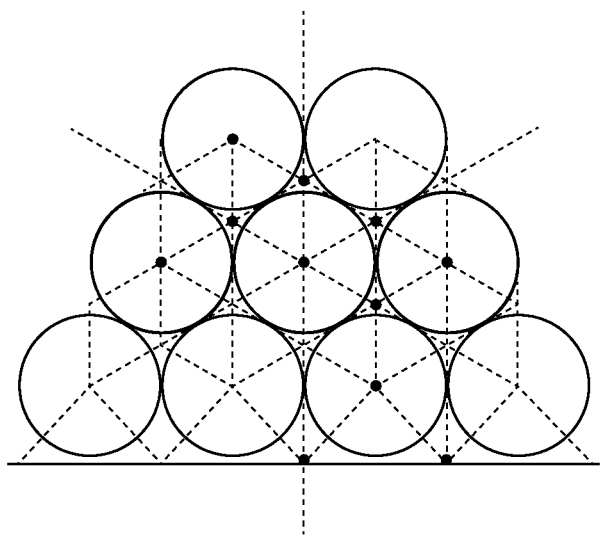
FIG. 39 is a sectional view of a three-layer solenoid inductor lining.
Figure 40:
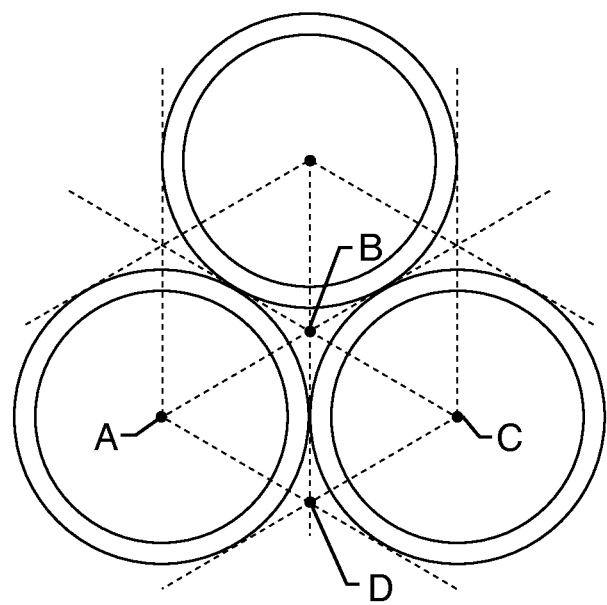
FIG. 40 is a sectional view of a basic cell ABCD representing the turn-to-turn capacitance.

FIGS. 39 and 40 are taken from a paper entitled, MODELING OF PARASITIC CAPACITANCE OF INDUCTORS by Antonio Massarini and Marian Kazimierczuk given at the 16$^{th}$ Annual Capacitor and Resistor Technology Symposium CARTS '96, Mar. 11-15, 1996 Monteleone Hotel, New Orleans, La. CARTS '96 is sponsored by the Components Technology Institute in cooperation with the IEEE and the Microelectronics Society. This paper will hereinafter be referred to as the "Massarini paper." The entire contents of the Massarini paper are incorporated herein by reference.

FIG. 39 is taken from FIG. 2 of the Massarini paper showing a cross-sectional view of a 3-layer solenoid inductor lining which is the same as previously illustrated herein in FIGS. 33, 34 and 35.

FIG. 40 is taken from FIG. 3 of the Massarini paper and shows a basic cell ABCD representing the turn-to-turn capacitance. The Massarini paper goes on to do a comprehensive mathematical analysis of the parasitic capacitances, including the capacitance of the air gaps. Massarini also calculates the total capacitance of the basic cell, the turn-to-turn capacitance and the overall straight capacitance. Accordingly, the Massarini reference gives a good way to approximate the total capacitance, which is very useful when designing the self-resonant tank filter of the present invention. There are alternative methods to model the self-resonant inductor and these include SEMCAD and other sophisticated electromagnetic modeling programs that are available in the art.

Figure 41:
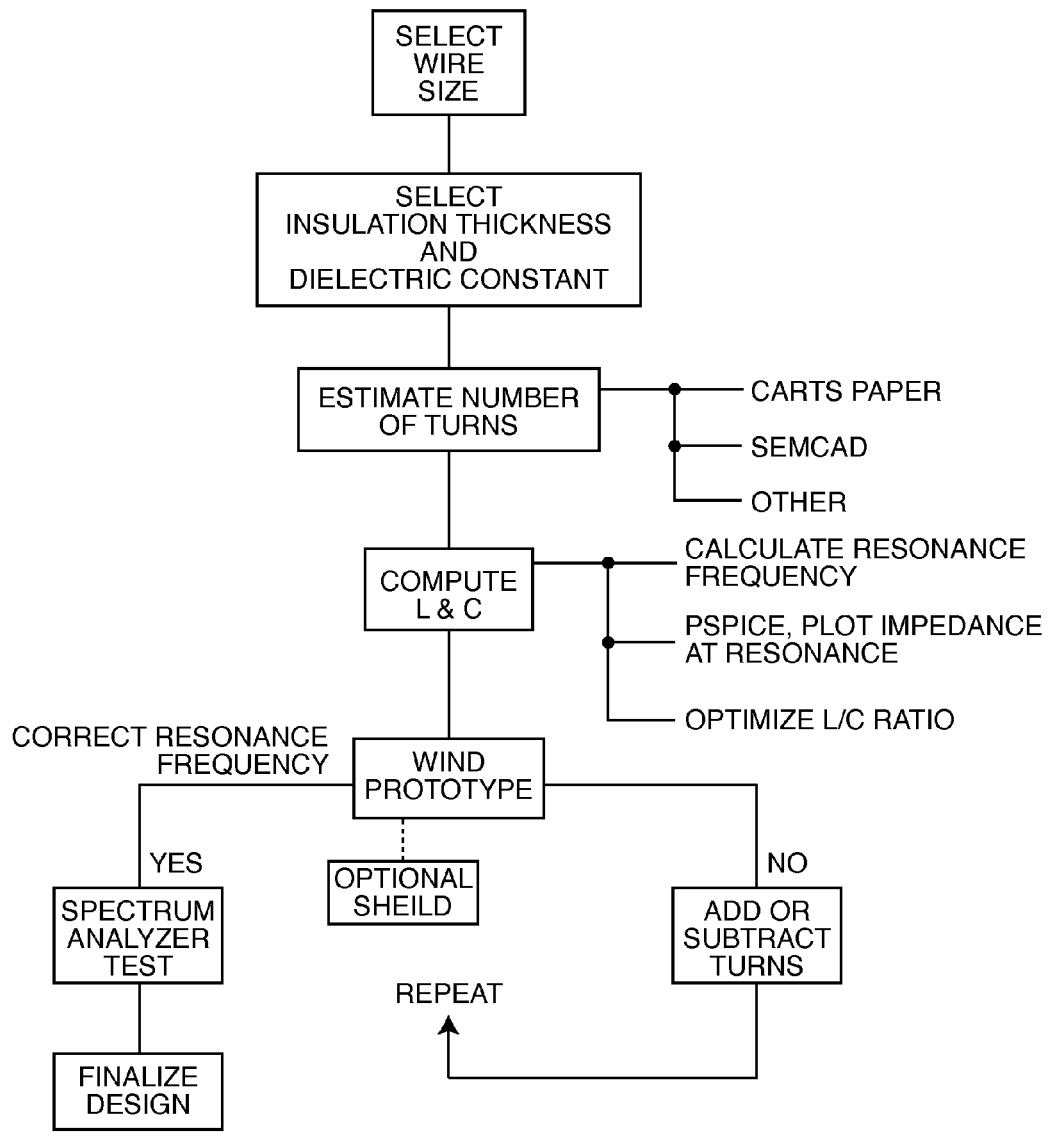
FIG. 41 is a flow chart illustrating the essential steps an engineer goes through in designing the self-resonant coil of the present invention.

FIG. 41 is a flow chart showing the essential steps one goes through in designing the self-resonant coil of the present invention. First of all, one selects the wire type and the wire size that will be used to wind the inductor structure. One then selects the type of insulation, the insulation thickness and in particular, its dielectric constant. One then uses the equations from the referenced Massarini paper, SEMCAD or another modeling program to estimate the number of turns required to come up with the proper inductance, the L/C ratio and the amount of capacitance. Once one knows the amount of inductance and the amount of capacitance, one can refer to FIG. 12 to calculate the resonant frequency. This is an iterative process as one selects the resonant frequency to be centered at MRI RF-pulsed frequency. For example, for a 1.5 Tesla scanner, one would select a resonant frequency $f_r$ approximately 64 MHz.

If the self-resonant coil is to be put inside an optional shield, then additional calculations would be made to also calculate parasitic capacitance to the shield and also the effect of the shield on the magnetic field surrounding the inductors. A more detailed discussion of how the shield can be used to properly tune a tank or bandstop filter of the present invention was disclosed in application Ser. No. 12/891,292 filed on Sep. 27, 2010 and published as number 2011/0054582. The contents of this application are incorporated in full herein with this reference.

One is referred to Paragraph 4.5 of Provisional Application Ser. No. 60/283,725, to which this application is a Continuation-in-Part Application. The last paragraph of this provisional patent application says, "a more effective way to cut the surface electrodes from the rest of the circuit would be to use a resonant circuit in place of the inductors in panel b. This resonant circuit would consist of an inductor in parallel with a capacitor (an LC circuit). If this LC circuit was tuned to the MRI frequency, it would create a very high impedance at this frequency. This will effectively cut the surface electrodes and reduce unwanted heating. For maximal effectiveness, the LC circuit should be shielded." Accordingly, the single or multilayer inductive coils of the present invention can be shielded.

Referring once again to FIG. 40, after one computes the amount of inductance and capacitance (either inside or outside the optional shield), then one winds prototypes. When winding the prototype inductor, one uses a Spectrum or a Network Analyzer to assess the resonant frequency and also the amount of the impedance at resonance. One may go back through the entire flow chart several times until one achieves the desired result, which is a resonant center frequency at the selected MRI RF-pulsed frequency, and also sufficient impedance to provide the required at least 15 dB of attenuation. Once the resonant frequency is verified in a Spectrum Analyzer, then the design is finalized. If it is not correct, the one can add or subtract turns until the desired result is achieved.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. An implantable lead, comprising:
  a) at least one lead conductor extending from a proximal conductor end to a distal conductor portion having a distal conductor end, wherein the proximal conductor end is configured to be removably connectable or non-removably connected to electronic circuits of a medical device;
  b) at least one electrode contactable with biological cells, wherein the electrode is electrically and physically connected to the distal conductor portion or the distal conductor end; and c) a self-resonant inductor physically and electrically in series at or proximally adjacent to the at least one electrode, wherein the self-resonant inductor is of a continuous length of the at least one lead conductor and comprises:
   i) a first insulated coiled portion of the continuous length of the lead conductor extending along a longitudinal axis in a distal direction from a first coiled portion proximal end to a first coiled portion distal end;
   ii) a second insulated coiled portion of the continuous length of the lead conductor extending along the longitudinal axis in a proximal direction from a second coil portion distal end adjacent to the first coiled portion distal end to a second coiled portion proximal end; and
   iii) a third insulated coiled portion of the continuous length of the lead conductor extending along the longitudinal axis in a distal direction from a third coiled portion proximal end adjacent to the second coiled portion proximal end to a third coiled portion distal end;
d) wherein the self-resonant inductor comprises parasitic capacitance between:
   i) axially extending and immediately adjacent surfaces of immediately adjacent ones of the first, second and third coiled portions of the continuous length of the lead conductor, and
   ii) the immediately adjacent first and second coiled portions and the immediately adjacent second and third coiled portions aligned substantially perpendicular to the longitudinal axis, and
   iii) the immediately adjacent first and second coiled portions and the immediately adjacent second and third coiled portions at an angle other than substantially perpendicular to the longitudinal axis,
e) wherein the self-resonant inductor is resonant at a first center frequency or across a range of frequencies about the first center frequency.

2. The lead of claim 1, wherein the self-resonant inductor is disposed inside a shield.

3. The lead of claim 2, wherein the self-resonant inductor comprises a parasitic capacitance between any or all of the first, second or third coiled conductors and the shield.

4. The lead of claim 3, wherein the self-resonant inductor comprises an equivalent circuit comprising an inductance in parallel with a capacitance.

5. The lead of claim 2, wherein the self-resonant inductor comprises an overall circuit Q within the shield and wherein the resultant 3-dB bandwidth is at least 128 kHz, so that the self-resonant inductor attenuates an RF current flow substantially about the first resonant center frequency that is at or near an MRI RF pulsed frequency.

6. The lead of claim 5, wherein the shield comprises a conductive electromagnetic shield.

7. The lead of claim 2, wherein the self-resonant inductor comprises a second resonant center frequency when removed from the shield and the first resonant center frequency within the shield, and wherein at least one of the inductance and the capacitance is adjusted to account for a shift between the first and second resonant center frequencies.

8. The lead of claim 1, wherein the first center frequency comprises an MRI RF pulsed frequency.

9. The lead of claim 8, wherein the self-resonant inductor has an inductance with an associated resistance and a parasitic capacitance with an associated resistance which inductance and parasitic capacitance and their respective resistances together determine a circuit Q having a resultant 3-dB bandwidth that is at least 128 kHz.

10. The lead of claim 9, wherein the circuit Q results in a 3-dB bandwidth that is on the order of megahertz.

11. The lead of claim 9, wherein the self-resonant inductor provides less than or equal to 3-dB of attenuation for a biological frequency range of 0-1 kHz.

12. The lead of claim 11, wherein the self-resonant inductor provides greater than or equal to 15-dB of attenuation at or near the MRI RF pulsed frequency.

13. The lead of claim 1, wherein the lead conductor is of a conductive material comprising an inner conductive core substantially surrounded by an outer conductive layer.

14. The lead of claim 13, wherein the outer conductive layer is biocompatible.

15. The lead of claim 13, wherein the outer conductive layer is selected from the group consisting of MP35N, nitinol, tungsten, tantalum, niobium, Co—Cr—Mo alloys, stainless steel alloys, stainless steel alloys with Mo, Ni, Cr combinations, carbon steels, and any combination thereof.

16. The lead of claim 13, wherein the inner conductive core is selected from the group consisting of silver, copper, platinum, platinum, platinum-iridium, platinum-tungsten, platinum alloys, tantalum, gold, palladium, nitinol, titanium, and titanium alloys.

17. The lead of claim 1, wherein the first, second and third coiled conductors are insulated with a dielectric coating selected from the group consisting of a thermoset, a thermoplastic coating, and a flexible coating.

18. The lead of claim 17, wherein the dielectric coating comprises a resin or modifier selected from the group consisting of pigments, plasticizers, filler particulates, flakes, spheres, nanoparticles, short fibers, long fibers, submicron fibers, isotropically dispersed submicron fibers, anistropically dispersed submicron fibers, laminate configurations, and any combination thereof.

19. The lead of claim 17, wherein the dielectric coating is selected from the group consisting of adhesives, elastomers, epoxies, fluoropolymers, copolymer blends, amorphous copolymer blends, semi-amorphous copolymer blends, copolymer blends with limited crosslinking, and any combination thereof.

20. The lead of claim 17, wherein the dielectric coating is selected from the group consisting of acrylonitrile butadiene styrene (ABS), acrylics, poly(methyl methacrylate) or PMMA, celluloids, acetates, cellulose acetate, ethylene-vinyl acetate, copolymers, cyclic olefin copolymer, polyethylene, poly(vinyl chloride), polystyrene, acetals, urethanes, carbothane, estane, pellethane, TECOFLEX®, TECOTHANE®, TEXIN®, nylons, Aesno, Besno, Nylon 6, Nylon 6,6, Nylon 12, VESTAMID®, polyether, polyester, polypropylene, polytetrafluoroethylene (PTFE), FEP, PFA, CTFE, ECTFE, PEEK, ETFE, PET, PBT, polyvinylidine fluoride (PVDF), ETTFE, THV, polycarbonate, polyetherimide, polysulfone, parylene, polyethylene, polypropylene, polyether block amides (PEBAX), acid copolymers, and any combination thereof.

21. The lead of claim 1, wherein the first coiled conductor is disposed radially inside the second coiled conductor, and wherein the second coiled conductor is disposed radially inside the third coiled conductor.

22. The lead of claim 1, wherein the lead conductor is of a conductive material selected from the group consisting of a cored tube, a clad tube, a plated tube, an electroplated tube, an anodized tube, and a filled tube.

23. The implantable lead of claim 1, wherein the self-resonant inductor is supported on a mandrel.

24. An elongate electrical medical lead, comprising:
a) at least one conductor with opposing proximal and distal conductor portions, wherein the proximal conductor portion is configured to be removably connectable or non-removably connected to electronic circuits of a medical device; and
b) at least one electrode contactable with biological cells, wherein the electrode is electrically and physically connected to the distal conductor portion or the distal conductor end,
c) wherein a continuous length of the at least one conductor comprises a first conductor section that extends in a first lengthwise direction along a longitudinal axis for a first physical length, then turns to define at least one reverse conductor section that extends in a substantially opposing lengthwise direction along the longitudinal axis for a second physical length, and then turns again to define a third conductor section that extends in the first lengthwise direction along the longitudinal axis for a third physical length,
d) wherein at least the first and reverse conductor sections or the reverse and third conductor sections are coiled conductor sections and have a parasitic capacitance between:
   i) axially extending and immediately adjacent surfaces of the immediately adjacent first and reverse coiled sections or the immediately adjacent reverse and third coiled sections of the continuous length of the lead conductor, and
   ii) at least one of the immediately adjacent first and reverse coiled sections and the immediately adjacent reverse and third coiled sections, as the case may be, aligned substantially perpendicular to the longitudinal axis, and
   iii) at least one of the immediately adjacent first and reverse coiled sections and the immediately adjacent reverse and third coiled sections, as the case may be, at an angle other than substantially perpendicular to the longitudinal axis;
e) wherein the at least first and reverse coiled conductor sections and the reverse and third coiled conductor sections, as the case may be, have an inductance with an associated resistance and the parasitic capacitance with an associated resistance which inductance and parasitic capacitance and their respective resistances together determine a circuit Q having a resultant 3-dB bandwidth that is at least 128 kHz.

25. The medical device of claim 24, wherein the at least one conductor comprising the first, reverse, and third conductor sections is disposed inside a shield.

26. The medical device of claim 25, wherein the at least one conductor comprises a parasitic capacitance between any of the first, reverse, and third conductor sections and the shield.

27. The medical device of claim 26, wherein the at least one conductor comprises an equivalent circuit comprising an inductance in parallel with a capacitance.

28. The medical device of claim 27, wherein the at least one conductor comprises an overall circuit Q within the shield and wherein the resultant 3-dB bandwidth is at least 128 kHz, so that the at least one conductor attenuates an RF current flow substantially about an MRI RF pulsed frequency.

29. The medical device of claim 25, wherein the shield comprises a conductive electromagnetic shield.

30. The medical device of claim 25, wherein the at least one conductor comprises a first resonant center frequency when removed from the shield and a second resonant center frequency within the shield, and wherein at least one of the inductance and the capacitance is adjusted to account for a shift between the first and second resonant center frequencies.

31. The medical device of claim 24, wherein the first, reverse, and third conductor sections comprise a continuous single length of conductive material.

32. The medical device of claim 31, wherein the continuous single length of conductive material is selected from the group consisting of a cored tube, a clad tube, a plated tube, an electroplated tube, an anodized tube, and a filled tube.

33. The medical device of claim 31, wherein the single length of conductive material comprises an inner conductive core substantially surrounded by an outer conductive layer, and wherein the outer conductive layer is biocompatible.

34. The medical device of claim 33, wherein the outer conductive layer is selected from the group consisting of MP35N, nitinol, tungsten, tantalum, niobium, Co—Cr—Mo alloys, stainless steel alloys, stainless steel alloys with Mo, Ni, Cr combinations, carbon steels, and any combination thereof.

35. The medical device of claim 33, wherein the inner conductive core is selected from the group consisting of silver, copper, platinum, platinum, platinum-iridium, platinum-tungsten, platinum alloys, tantalum, gold, palladium, nitinol, titanium, and titanium alloys.

36. The medical device of claim 24, wherein the first, reverse, and third conductor sections are insulated with a dielectric coating selected from the group consisting of a thermoset coating, a thermoplastic coating, and a flexible coating.

37. The medical device of claim 36, wherein the thermoset dielectric coating is selected from the group consisting of a resin or modifier comprising pigments, plasticizers, filler particulates, flakes, spheres, nanoparticles, short fibers, long fibers, submicron fibers, isotropically dispersed submicron fibers, anistropically dispersed submicron fibers, laminate configurations, and any combination thereof.

38. The medical device of claim 36, wherein the dielectric coating is selected from the group consisting of adhesives, elastomers, epoxies, fluoropolymers, copolymer blends, amorphous copolymer blends, semi-amorphous copolymer blends, copolymer blends with limited crosslinking, and any combination thereof.

39. The medical device of claim 36, wherein the dielectric coating is selected from the group consisting of acrylonitrile butadiene styrene (ABS), acrylics, poly(methyl methacrylate) or PMMA, celluloids, acetates, cellulose acetate, ethylene-vinyl acetate, copolymers, cyclic olefin copolymer, polyethylene, polyvinyl chloride), polystyrene, acetals, urethanes, carbothane, estane, pellethane, TECOFLEX®, TECOTHANE®, TEXIN®, nylons, Aesno, Besno, Nylon 6, Nylon 6,6, Nylon 12, VESTAMID®, polyether, polyester, polypropylene, polytetrafluoroethylene (PTFE), FEP, PFA, CTFE, ECTFE, PEEK, ETFE, PET, PBT, polyvinylidine fluoride (PVDF), ETTFE, THV, polycarbonate, polyetherimide, polysulfone, parylene, polyethylene, polypropylene, polyether block amides (PEBAX), acid copolymers, and any combination thereof.

40. The medical device of claim 24, wherein at least one of the first, reverse, and third conductor sections extends under, over or through a neighboring conductor section.

41. The medical device of claim 24, wherein at least one of the first, reverse, and third conductor sections resides proximate to and outside of a coiled portion of another conductor section.

42. The implantable lead of claim 24, wherein the first, reverse, and third conductor sections are supported on a mandrel.

43. An implantable lead, comprising:
a) at least one lead conductor extending from a proximal conductor end to a distal conductor portion having a distal conductor end, wherein the proximal conductor end is configured to be removably connectable or non-removably connected to electronic circuits of a medical device;
b) at least one electrode contactable with biological cells, wherein the electrode is electrically and physically connected to the distal conductor portion or the distal conductor end; and
c) a self-resonant inductor physically and electrically in series at or proximally adjacent to the at least one electrode, wherein the self-resonant inductor is of a continuous length of the at least one lead conductor and comprises:
    i) a first insulated coiled layer of the continuous length of the lead conductor extending along a longitudinal axis in a distal direction from a first coiled layer proximal end to a first coiled layer distal end;
    ii) a second insulated coiled layer of the continuous length of the lead conductor extending along the longitudinal axis in a proximal direction from a second coiled layer distal end adjacent to the first coiled layer distal end to a second coiled layer proximal end; and
    iii) a third insulated coiled layer of the continuous length of the lead conductor extending along the longitudinal axis in a distal direction from a third coiled layer proximal end adjacent to the second coiled layer proximal end to a third coiled layer distal end;
d) wherein the self-resonant inductor comprises parasitic capacitance between:
    i) axially extending and immediately adjacent surfaces of immediately adjacent ones of the first, second and third coiled layers of the continuous length of the lead conductor, and
    ii) the immediately adjacent first and second coiled layers and the immediately adjacent second and third coiled layers aligned substantially perpendicular to the longitudinal axis, and
    iii) the immediately adjacent first and second coiled layers and the immediately adjacent second and third coiled layers at an angle other than substantially perpendicular to the longitudinal axis, and
e) wherein the self-resonant inductor is resonant at a center frequency or across a range of frequencies about the center frequency,
f) wherein the center frequency is at or near an MRI RF pulsed frequency, and
g) wherein a resultant 3-dB bandwidth of the self-resonant inductor is at least 128 kHz.

44. The lead of claim 43, wherein the self-resonant inductor is disposed inside a shield.

45. The lead of claim 44, wherein the shield comprises a conductive electromagnetic shield.

46. The lead of claim 43, wherein the first coiled conductor layer is electrically connected to the second coiled conductor layer, and wherein the second coiled conductor layer is electrically connected to the third coiled conductor layer.

47. The lead of claim 43, wherein the first coiled conductor layer is disposed radially inside the second coiled conductor layer, and wherein the second coiled conductor layer is disposed radially inside the third coiled conductor layer.

48. The lead of claim 43, wherein a dielectric coating surrounds at least a portion of the first, second and third coiled conductor layers.

49. The lead of claim 43, wherein the first, second and third coiled conductor layers comprise a continuous single length of conductive material.

50. The lead of claim 43, wherein the self-resonant inductor provides less than or equal to 3-dB of attenuation for a biological frequency range of 0-1 kHz, and wherein the self-resonant inductor provides greater than or equal to 15-dB of attenuation at or near the MRI RF pulsed frequency.

51. The implantable lead of claim 43 wherein the second coiled conductor proximal end is adjacent to the first coiled conductor proximal end and wherein the third coiled conductor distal end is adjacent to the second coiled conductor distal end.

52. The implantable lead of claim 43, wherein the self-resonant inductor is supported on a mandrel.

53. An implantable lead, comprising:
a) at least one lead conductor extending from a proximal conductor end to a distal conductor portion having a distal conductor end, wherein the proximal conductor end is configured to be removably connectable or non-removably connected to electronic circuits of a medical device;
b) at least one electrode contactable with biological cells, wherein the electrode is electrically and physically connected to the distal conductor portion or the distal conductor end; and
c) a self-resonant inductor in series at or proximally adjacent to the at least one electrode, wherein the self-resonant inductor is of a continuous length of the at least one lead conductor and comprises:
    i) two or more even number of insulated coiled layers of the continuous length of the lead conductor extending proximally and distally from a first location to a second location along a longitudinal axis; and
    ii) a return conductor electrically and physically connected to the electrode;
d) wherein the self-resonant inductor comprises parasitic capacitance between:
    i) axially extending and immediately adjacent surfaces of two immediately adjacent coiled layers of the two or more even number of coiled layers of the continuous length of the lead conductor, and
    ii) the two immediately adjacent coiled layers aligned substantially perpendicular to the longitudinal axis, and
    iii) the two immediately adjacent coiled layers at an angle other than substantially perpendicular to the longitudinal axis,
e) wherein the self-resonant inductor is resonant at or near an MRI RF pulsed frequency, and
f) wherein the self-resonant inductor has an inductance with an associated resistance and the parasitic capacitance with an associated resistance which inductance and parasitic capacitance and their respective resistances together provide a circuit Q having a resultant 3-dB bandwidth that is at least 128 kHz.

54. The lead of claim 53, wherein the circuit Q results in a 3-dB bandwidth that is on the order of megahertz.

55. The lead of claim 53, wherein the self-resonant inductor provides less than or equal to 3-dB of attenuation for a biological frequency range of 0-1 kHz.

56. The lead of claim 53, wherein the self-resonant inductor provides greater than or equal to 15-dB of attenuation at or near the MRI RF pulsed frequency.

57. The lead of claim 53, wherein the self-resonant inductor is disposed inside an electromagnetic shield, wherein the self-resonant inductor comprises a parasitic capacitance between its adjacent turns and between any of the two or more even number of layers of the coiled conductors and the shield, and wherein the self-resonant inductor comprises an equivalent circuit including an inductance in parallel with a capacitance along with their associated resistances, and wherein the self-resonant inductor comprises a first resonant center frequency when removed from the shield and a second resonant center frequency within the shield, wherein at least one of the inductance and the capacitance is adjusted to account for a shift between the first and second resonant center frequencies, and wherein the self-resonant inductor attenuates the MRI RF pulsed frequency substantially about the second resonant center frequency.

58. The implantable lead of claim 53, wherein the self-resonant inductor is supported on a mandrel.

59. An implantable lead, comprising:
 a) a lead conductor having a length extending from a proximal conductor end to a distal conductor portion having distal conductor end; and
 b) at least one electrode contactable with biological cells, wherein the electrode is electrically and physically connected to the distal conductor portion or the distal conductor end; and
 c) a self-resonant inductor physically and electrically in series with the electrode, the self-resonant inductor comprising a dielectric coating substantially surrounding a continuous length of the at least one lead conductor, wherein the self-resonant inductor comprises
   three or more odd number of insulated coiled layers of the continuous length of the lead conductor extending either proximally or distally along a longitudinal axis,
 d) wherein the self-resonant inductor comprises a parasitic capacitance between:
  i) axially extending and immediately adjacent surfaces of two immediately adjacent coiled layers of the three or more odd number of coiled layers of the continuous length of the lead conductor, and
  ii) the two immediately adjacent coiled layers aligned substantially perpendicular to the longitudinal axis, and
  iii) the two immediately adjacent coiled layers at an angle other than substantially perpendicular to the longitudinal axis, and
 d) wherein the self-resonant inductor has an inductance with an associated resistance and the parasitic capacitance with an associated resistance which inductance and parasitic capacitance and their respective resistances together provide a circuit Q having a resultant 3-dB bandwidth that is at least 128 kHz.

60. The implantable lead of claim 59, wherein the self-resonant inductor is supported on a mandrel.

61. The lead of claim 59, wherein the circuit Q results in a 3-db bandwidth that is on the order of megahertz.

62. The lead of claim 59, wherein the self-resonant inductor provides less than or equal to 3-dB of attenuation for a biological frequency range of 0-1 kHz.

63. The lead of claim 59, wherein the self-resonant inductor provides greater than or equal to 15-dB of attenuation at or near the MRI RF pulsed frequency.

64. The lead of claim 59, wherein the self-resonant inductor is disposed inside an electromagnetic shield, wherein the self-resonant inductor comprises a parasitic capacitance between its adjacent turns and between any of the three or more odd number of layers of coiled conductors and the shield, and wherein an equivalent circuit of the self-resonant inductor comprises an inductance in parallel with a capacitance along with their associated resistances, and wherein the self-resonant inductor comprises a first resonant center frequency when removed from the shield and a second resonant center frequency within the shield, wherein at least one of the inductance and the capacitance is adjusted to account for a shift between the first and second resonant center frequencies, and wherein the self-resonant inductor attenuates the MRI RF pulsed frequency substantially about the second resonant center frequency.

65. An implantable lead, comprising:
 a) at least one lead conductor extending from a proximal conductor end to a distal conductor portion having a distal conductor end, wherein the proximal conductor end is configured to be removably connectable or non-removably connected to electronic circuits of an active implantable medical device;
 b) at least one electrode contactable with biological cells, wherein the electrode is electrically and physically connected to the distal conductor portion or the distal conductor end; and
 c) a self-resonant inductor physically and electrically in series at or proximally adjacent to the at least one electrode, wherein the self-resonant inductor is of a continuous length of the at least one lead conductor and comprises at least two insulated coiled conductors, and wherein:
  i) a first one of the at least two insulated coiled portions of the continuous length of the lead conductor extends along a longitudinal axis in a distal direction from a first coiled portion proximal end to a first coiled portion distal end;
  ii) a return conductor extends in a proximal direction from a return conductor distal end connected to the first coiled portion distal end to a return conductor proximal end; and
  iii) a second one of the at least two insulated coiled portions of the continuous length of the lead conductor extends along the longitudinal axis in a distal direction from a second coiled portion proximal end adjacent to the return conductor proximal end to a second coiled portion distal end;
 d) wherein the self-resonant inductor comprises parasitic capacitance between:
  i) axially extending and immediately adjacent surfaces of the immediately adjacent first and second coiled portions of the continuous length of the lead conductor, and
  ii) the immediately adjacent first and second coiled portions aligned substantially perpendicular to the longitudinal axis, and
  iii) the immediately adjacent first and second coiled portions at an angle other than substantially perpendicular to the longitudinal axis,
 e) wherein the self-resonant inductor is resonant at a first center frequency or across a range of frequencies about the first center frequency.

66. The implantable lead of claim 65, wherein the return conductor resides inside the at least two insulated coiled conductors.

67. The implantable lead of claim 65, wherein the return conductor resides between the first and second insulated coiled conductors.

68. The implantable lead of claim 65, wherein the self-resonant inductor is supported on a mandrel.

69. An implantable lead, comprising:
 a) at least one lead conductor extending from a proximal conductor end to a distal conductor portion having a distal conductor end, wherein the proximal conductor end is configured to be removably connectable or non-removably connected to electronic circuits of an active implantable medical device;
b) at least one electrode contactable with biological cells, wherein the electrode is electrically and physically connected to the distal conductor portion or the distal conductor end; and
c) a self-resonant inductor physically and electrically in series at or proximally adjacent to the at least one electrode, wherein the self-resonant inductor comprises at least two insulated coiled portions of a continuous length of the lead conductor, and wherein:
  i) a first one of the at least two insulated coiled portions of the continuous length of the lead conductor extends along a longitudinal axis in a distal direction from a first coiled portion proximal end to a first coiled conductor distal end; and
  ii) a second one of the at least two insulated coiled portions of the continuous length of the lead conductor extends in a proximal direction from a second coil portion distal end adjacent to the first coiled portion distal end to a second coiled portion proximal end;
d) wherein the self-resonant inductor comprises a total parasitic capacitance between:
  i) axially extending and immediately adjacent surfaces of the immediately adjacent first and second coiled portions of the continuous length of the lead conductor, and
  ii) the immediately adjacent first and second coiled portions aligned substantially perpendicular to the longitudinal axis, and
  iii) the immediately adjacent first and second portions at an angle other than substantially perpendicular to the longitudinal axis,
e) wherein the self-resonant inductor is resonant at a first center frequency or across a range of frequencies about the first center frequency.

70. The implantable lead of claim 69, wherein the self-resonant inductor is supported on a mandrel.

* * * * *